(12) United States Patent
Svorc et al.

(10) Patent No.: US 6,340,597 B1
(45) Date of Patent: *Jan. 22, 2002

(54) ELECTROCHEMICAL BIOSENSORS AND PROCESS FOR THEIR PREPARATION

(75) Inventors: Josef Svorc, Prievidza; Stanislav Miertus, Bratislava; Miroslav Stredansky, Modra, all of (SK)

(73) Assignee: Saicom S.r.l. (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/001,695

(22) PCT Filed: Jul. 3, 1996

(86) PCT No.: PCT/EP96/02919

§ 371 Date: Dec. 31, 1997

§ 102(e) Date: Dec. 31, 1997

(87) PCT Pub. No.: WO97/02359

PCT Pub. Date: Jan. 23, 1997

(30) Foreign Application Priority Data

Jul. 5, 1995 (IT) .......................................... MI95A1441

(51) Int. Cl.⁷ ........................ G01N 27/00; G01N 27/02; G01N 33/53; C12Q 1/00; C12Q 1/68
(52) U.S. Cl. ................. 436/518; 422/82.01; 422/82.02; 435/4; 435/6; 435/7.1; 435/25; 435/26; 435/820; 436/518; 436/532; 204/153.12; 204/402; 204/403; 204/435
(58) Field of Search ........................ 422/82.01, 82.02; 435/4, 6, 7.1, 820, 25, 26; 436/518, 535; 204/402, 403, 435, 153.12

(56) References Cited

U.S. PATENT DOCUMENTS 5,269,891 A * 12/1993 Colin ..................... 204/153.12

FOREIGN PATENT DOCUMENTS

EP 415 124 A2 * 3/1991
EP 563 795 A1 * 10/1993

OTHER PUBLICATIONS

Hackh's Chemical Dictionary, 4th edition, McGraw–Hill Co., New York, pp. 488–489, "Paraffins". 1969.*

C. Peht et al., "Preparation and characterization of a new enzyme electrode based on solid paraffin and activated graphite particles," Talanta 42:1783–9, 1995.*

J. Wang et al., "Polishable and Robust Biological Electrode Surfaces", Anal. Chem. 62:318–320. 1990.*

* cited by examiner

Primary Examiner—Jennifer Graser
Assistant Examiner—Ja-Na Hines
(74) Attorney, Agent, or Firm—Hedman, Gibson & Costigan, P.C.

(57) ABSTRACT

The present invention concerns new electrochemical biosensors for the determination of analytes concentration in sample solutions or suspensions, based on composite transducers containing an electro-conducting material, in the form of powder or grains, a chemical mediator, optionally a substance capable of sorption of said chemical mediator, and a solid binding maker, which is a compound in solid state at room temperature; said biosensors are prepared by incorporating a biocatalyst into the bulk of said composite transducers or by applying a biocatalytic layer onto their surface.

24 Claims, 19 Drawing Sheets

ELECTROCHEMICAL BIOSENSORS AND PROCESS FOR THEIR PREPARATION

The present application is the national stage filing of and claims priority to International Application No. PCT/EP96/02919, filed Jul. 3, 1996 and Italian Application Serial No. MI95A001441 filed Jul. 5, 1995.

FIELD OF THE INVENTION

The present invention concerns new electrochemical biosensors based on composite transducers containing solid binding makers, prepared by incorporating a biocatalyst into the bulk of said transducers or by applying a biocatalytic layer onto the surface of said transducers. The biosensors of the invention are useful in the determination of the concentration of specific analytes in sample solutions or suspensions.

PRIOR ART DISCLOSURE

A biosensor is a device incorporating a biological sensing element either intimately connected to or integrated within a transducer. Its usual aim is to produce electronic signals which are proportional to the concentration of the specific substance which has to be determined.

Analytical advantages of biosensors consist in their specificity, sensitivity, simple manipulation, rapid response and consequent low costs of analysis. These specific and sensitive devices have been used in medical diagnostics, in monitoring food quality and freshness, in environmental monitoring, in fermentation and analytical control, and so on.

Electrochemical biosensors, especially amperometric ones, play a significant role in the applications of these devices. Amperometric biosensors of the second generation, based on redox reactions, are characterized by the use of chemical mediators instead of molecular oxygen. During the transformation of a substrate by a bioactive material, chemical mediators shuttle electrons from the redox centre of the biocatalyst itself to the indicating electrode and the corresponding amperometric signal is measured. One of the most promising groups of chemical mediators consists of metallocenes, and in particular ferrocenes. The first successful enzyme electrode based on ferrocene was prepared by Cass et al. (*Anal. Chem.* 56, 667–671, 1984); in this glucose sensitive sensor, the electrode was prepared by soaking a spongy carbon foil with 1,1'-dimethyl-ferrocene and the enzyme glucose oxidase was chemically immobilized on the surface of this electrode.

Later on, Dicks et al. (*Ann. Biol. Clin.* 47, 607–619, 1989) prepared a gold microelectrode covered with a polypyrrol film, on which glucose oxidase and ferrocene were adsorbed. However, these electrodes, having chemical mediators adsorbed on the surface of the device, show poor stability due to the leaking of the mediators out of the transducer.

Since the late 1980s, intensive research activities were devoted to the development of biosensors based on Carbon Paste Electrodes (CPE); a carbon paste electrode is a mixture of electrically conducting graphite or carbon with a pasting liquid, e.g. paraffin oil, silicon oil, Nujol etc.

This kind of electrodes has the advantage of allowing bulk modification of the eletrode material with biocatalysts, as well as with other advantageous components, essential for the effective functioning of the device. Furthermore, bulk modification allows to create sensors with renewable surfaces, so that each measurement can be performed on a new surface of the electrode, thus avoiding the drawbacks due to previuos measurement residuals.

A CPE is commonly prepared by mixing carbon or graphite powder with a biocatalyst, a chemical mediator and optionally a co-factor, and by finally adding one of the above mentioned pasting liquids. The thus obtained paste is packed in a suitable tube, so to obtain a disc electrode (L. Gorton, *Electroanalysis*, 7, 23–45, 1995). These biosensors can be used for the detection of different analytes, such as glucose, fructose, galactose, ethanol, glycerol, aminoacids, lactate, xanthines etc., and are based on the corresponding oxidases and co-factor dependent dehydrogenases.

Nevertheless, CPE based biosensors show the following practical drawbacks and limitations:
i) poor mechanical properties, due to their paste creamy character imparted by the pasting liquid, often leading to easy disintegration of the system;
ii) poor compatibility of the paste with the biocatalytic enzyme, due to their opposite chemical properties (an enzyme is usually hydrophilic, while paste is strongly hydrophobic), often leading to phase separation (biocatalyst/transducer);
iii) leaking of the mediator out of the CPE, due to poor compatibility of CPE with the mediator.

Finally, the above mentioned features of CPE hinder or significantly reduce the electron transfer from the biocatalytic site to the electrode.

In alternative to the use of paste matrices for the fabrication of composite enzyme electrodes, direct modification of enzymes with chemical mediators was carried out by A. E. G. Cass and M. H. Smit (Trends in Electrochemical Biosensors, G. Costa e S. Miertus Ed., *Word Sci. Publ.*, 25–42, 1992); in order to prevent the mediator leaking out of the transducer, peroxidase was covalently modified with ferrocenyl groups, by derivatizing the enzyme chains near the active redox centre.

Furthermore, Karube et al. recently described enzyme-immobilized electrodes based on electrically conducting enzymes (EPA 0 563 795), i.e. enzymes to which electrical conductivity is imparted by covalently linking a chemical mediator. The electrical conductivity of such enzymes varies depending upon the amount of presence of the substrate to be detected in a specimen sample. Chemical mediators can be attached through a covalent bond to enzymes, such as oxidases or dehydrogenases, either to the proteic body (for example, to an aminic group of a lysine residue) or to a side chain of the enzyme (for example, to an oligosaccharide chain, to an alkyl chain, to a peptidic chain linked to the main chain, etc.).

Nevertheless, the covalent attachment of a mediator to the enzyme has the great disadvantage of changing the electrochemical properties of the mediator itself, consequently reducing its mobility and affecting its reaction rate with the enzyme. Moreover, the procedures and operative conditions used in the modification of enzymes are rather drastic for biocatalysts; chemical modification can significantly reduce enzyme activity and stability, leading to a consequent decrease or total loss of activity, when naturally low-stable enzymes are used. Furthermore, said chemical modification leads to an increase of production costs.

Therefore, it is felt the need of devising alternative electrochemical biosensors, endowed with higher stability and efficacy with respect to the known devices.

SUMMARY OF THE INVENTION

Now, the Applicant has unexpectedly found new electrochemical biosensors based on composite transducers, comprising at least a solid binding maker, as defined hereunder, able to overcome the drawbacks of the prior art.

The biosensors of the invention comprise:
a) at least an electro-conducting material, in the form of powder or grains;
b) at least a chemical mediator;
c) optionally, a substance capable of sorption of said chemical mediator;
d) at least a solid binding maker, which is a compound in solid state at room temperature, selected from the group consisting of: linear or branched, saturated or unsaturated hydrocarbons, containing from 12 to 60 carbon atoms, preferably from 12 to 30 carbon atoms, optionally substituted with at least a group selected from —OH, —SH, —NH2, —CO—, —CHO, —SO3H, —COOH, —OR1, —SR1, —NR1R2 and —COOR1, wherein R1 and R2 are independently hydrocarbon groups $C_1$–$C_{30}$, optionally containing one or more heteroatoms; esters of fatty acids with glycerol; and esters of fatty acids with cholesterol; and
e) at least a biocatalyst, selected from the group consisting of enzymes, cells, cellular components, tissues, immunoproteins and DNA.

In the biosensors of the invention, said biocatalyst (e) can be either incorporated into the body of the composite transducer, made up of components (a)–(d), or applied onto the surface of said composite transducer, in the form of a film layer.

The biosensor of the invention can be optionally covered by a suitable membrane. When said biocatalyst is an enzyme requiring the presence of the corresponding co-factor, the biosensors of the invention comprise even said co-factor.

Furthermore, the present invention concerns a process for the preparation of a biosensor as described above, comprising the following steps:
1) mixing said electro-conducting material with said chemical mediator;
2) optionally mixing the mixture obtained in step (1) with said substance capable of sorption of the chemical mediator;
3) optionally mixing the mixture obtained in step (1) or (2) with said biocatalyst;
4) suitably mixing the mixture obtained in step (1), (2) or (3) with said solid binding maker;
5) introducing and optionally pressing the mixture obtained in step (4) in a suitable holder, thus obtaining a compact form;
6) when step (3) is not worked out, applying a biocatalytic layer onto the surface of the transducer obtained in step (5);
7) optionally covering the biosensor obtained in step (5) or (6) with a suitable membrane.

A further object of the present invention is a procedure for the determination of analytes concentration in sample solutions or suspensions, comprising applying suitable electrode potential, contacting the biosensor of the invention with said sample solutions or suspensions and finally masuring current changes, which are proportional to the concentration of the analyte.

DESCRIPTION OF THE DRAWINGS

FIG. 1 shows a preferred embodiment of a biosensor according to the present invention, wherein the composite transducer 2 is cylindrically shaped and is allocated in an envelope 1, made up of a glass or plastic cylinder; a membrane or net 4 can fix the biocatalyst to the transducer 2.

DETAILED DESCRIION OF THE INVENTION

Figure 1A:
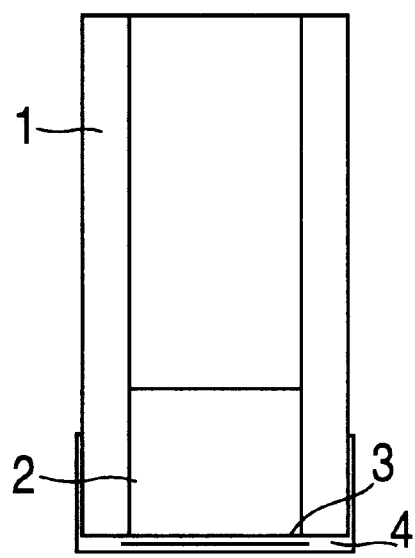
FIG. 1A, said biocatalyst is applied onto the surface of said transducer 2 in the form of a layer 3.

The characteristics and the advantages of the new electrochemical biosensors based on new composite transducers, according to the present invention, will be better reported in the following detailed description.

The biosensors according to the present invention are capable of quantitatively determining a specific analyte contained in a sample, such as a solution or a suspension, in a rapid and easy manner; furthermore, said biosensors show good mechanical properties, particularly compactness and plasticity, and do not disgregate during the use. These advantages are mainly due to the use of solid binding maker as essential innovative component of the transducer, giving solid compact mixtures with high stability, efficient communication between redox center and electrode, stability of the biocatalyst and retention of the chemical mediator, thus overcoming carbon paste drawbacks of the prior art.

According to a preferred embodiment of the biosensors according to the present invention, said electro-conducting material, said chemical mediator, said solid binding maker and optionally said substance capable of sorption of said chemical mediator are mixed together and pressed to give the composite transducer, in the form of a compact solid mixture. The biocatalyst can be either incorporated into the bulk of said composite transducer or applied onto the transducer surface in the form of a film layer.

According to another embodiment of the biosensors of the invention, the composite transducer does not contain the chemical mediator, which is directly added to the sample solution or suspension to be tested.

Alternatively, said chemical mediator can be contained, at the same time, in the composite transducer and in the sample solution or suspension.

Said electro-conducting material, in the form of powder or grains, is preferably selected from the group consisting of metals, such as gold, platinum, palladium, iridium, and their alloys, carbon and graphite. This electro-conducting material has preferably a granulometry ranging from 0.05 to 200 µm.

Said chemical mediator is one of the natural and synthetic mediators commonly used in the biosensors known in art, and is preferably selected from the group consisting of cytochromes, quinones, aminophenols, electron acceptor aromatic compounds (e.g. TTF=tetrathiafulvalene and NMP=N-methylphenazinium), electron donor aromatic compounds (e.g. TCNQ=tetracyano-p-quinodimethane), organic conducting salts (e.g. TTF.TCNQ=tetrathiafulvalene 7,7,8,8-tetracyano-p-quinodimethane and NMP.TCNQ=N-methylphenazinium 7,7,8,8-tetracyano-p-quinodimethane), organic dyes, metallocenes, organometallic complexes of Os, Ru and V, inorganic complexes of Fe. More preferably, said chemical mediator is ferrocene, 1,1'-dimethyl-ferrocene, hexacyanoferrate (II) or hexacyanoferrate (III).

Said substance capable of sorption of the chemical mediator is any substance having adsorption and ionic-exchange properties, preferably selected from the group consisting of silica, alumina, zeolites and Nafion®, a perfluorinated ion exchange powder prepared from a copolymer of tetrafluor-ethylene and perfluoro(2-(fluorosulfonylethoxy)propyl vinyl ether which is commercially available. Said substance is optionally contained in the composite transducer of the biosensor according to the present invention; its presence is preferred in case of prolonged and multiple use of the biosensor itself.

Said solid binding maker is a compound which is in solid state at room temperature, having a melting point preferably comprised between 25 and 200° C., and more preferably between 35 and 90° C. (in particular, having a melting point of 25–90° C. for bulk biosensors, and of 25–200° C. for biosensors having a biocatalytic layer applied onto their surface).

Said solid binding maker belongs to one of the following classes:
i) linear or branched, saturated or unsaturated hydrocarbons, containing from 12 to 60 carbon atoms, preferably from 12 to 30 carbon atoms, optionally substituted with at least a polar group selected from —OH, —SH, —NH2, —CO—, —CHO, —SO3H, —COOH, —OR1, —SR1, —NR1R2 and —COOR1, wherein R1 and R2 are independently hydrocarbon groups $C_1$–$C_{30}$, optionally containing one or more heteroatoms;
ii) esters of fatty acids with glycerol;
iii) esters of fatty acids with cholesterol.

When the solid binding maker belongs to class (i), it is preferably hexadecanol, hexadecanone, tetradecylamine, eicosane or tetracosane.

When the solid binding maker belongs to class (ii), it is preferably a mono, bi or triester of glycerol with fatty acids containing from 12 to 24 carbon atoms; more preferably, said solid binding maker is monostearoyl glycerol or lecithin.

When the solid binding maker belongs to class (iii), it is preferably an ester of cholesterol with a fatty acid containing from 12 to 24 carbon atoms; more preferably, said solid binding maker is cholesteryl myristate, cholesteryl stearate or cholesteryl oleate.

Said solid binding maker plays a leading role in the composition of the composite transducer of the biosensors of the invention; in fact, said compound is capable of imparting improved mechanical properties to the transducer itself, especially compactness and plasticity, in comparison with the common carbon pastes of the prior art, where pasting liquids were used. Furthermore, said solid binding makers ensure a higher compatibility with the biocatalyst and the chemical mediator; moreover, their are capable of exerting an action in support of the substances capable of sorption of the chemical mediator (the presence of which is only optional), thus accounting to physical immobilisation of both the biocatalyst and the chemical mediator.

Said solid binding maker is also able to secure a suitable molecular environment within the transducer body, which allows an efficient electron transfer among the redox centre of the biocatalyst, the chemical mediator and the conducting material, and subsequently great effectivity of the biocatalytic process, high conductivity and stability, during both storage and use.

Finally, thanks to said solid binding makers, it is possible to obtain solid-state transducers according to the desired forms and shapes; the absence of these binding makers leads to a drastic reduction of the biosensor performance and to the loss of its mechanical properties.

Said biocatalyst can be constituted of one or more enzymes able to catalyse a redox reaction, cells, cellular components, tissues, immunoproteins or DNA.

Preferably, said biocatalyst belongs to one of the following classes:
enzymes, preferably selected from the group consisting of glucose oxidase, galactose oxidase, glycollate oxidase, alcohol oxidase, cholesterol oxidase, polyphenyl oxidase, ascorbate oxidase, lipoxygenase, lipoxidase, peroxidase, catalase, xanthine oxidase, pyruvate oxidase, β-galactosidase, invertase, cholinesterase, citrate lyase, amylases and mixtures thereof;
enzymes which require the presence of a co-factor, in association with said co-factor, preferably selected from the group consisting of glucose dehydrogenase, alcohol dehydrogenase, fructose dehydrogenase, malate dehydrogenase, lactate dehydrogenase, mannitol dehydrogenase, glycerol dehydrogenase, isocitrate dehydrogenase, galactose dehydrogenase, glucose phosphate dehydrogenase, tartrate dehydrogenase and mixtures thereof;
cells, preferably selected from the group consisting of *Gluconobacter oxidans, Escherichia coli, Aspergillus niger, Pseudomonas fluorescens, Trichosporon brassicae, Saccharomices cerevisiae, Breviacterium lactofermentum, Enterobacter agglomerans, Leuconostoc mesenteroides, Nocardia erythropolys* and mixtures thereof;
immunoproteins and immunosystems based on antibodies labelled by enzymes.

When the enzyme requires the presence of a co-factor, said co-factor is preferably selected from the group consisting of NAD, NADH, NADP, NADPH, FAD, FMN and quinones. The co-factor is contained, as well as the corresponding enzyme, in the biosensor of the invention.

In particular, according to a specific embodiment, both the enzyme and the corresponding co-factor can be contained in the bulk of said biosensor; alternatively, both the enzyme and the corresponding co-factor can be applied onto the surface of said transducer, in the form of a layer; otherwise, the enzyme can be applied as a layer onto the surface of said transducer, while the corresponding co-factor is incorporated in the body of the transducer itself.

The biosensors of the invention can be optionally covered with a suitable membrane. Said membrane can be one of the different types of dialysis membranes known in the state of the art, preferably based on cellulose acetate or cellophane®, or it can be a membrane based on nitrocellulose, PVC, Teflon®, nylon, polycarbonates or polyesters. The quantitative composition of the above described composite transducer, with reference to 100 parts by weight of the composite transducer itself, composed of components (a)–(d), is as follows:
a) electro-conducting material: from 20 to 80%, and preferably from 30 to 60% by weight;
b) chemical mediator: from 0.5 to 30%, and preferably from 1 to 10% by weight;

c) substance capable of sorption of said chemical mediator: from 0 to 30%, and preferably from 1 to 20% by weight. When said substance is silica, alumina or zeolites, from 0 to 30%, and preferably from 5 to 20% by weight; when said substance is Nafion®, from 0 to 5%, and preferably from 1 to 3% by weight;

d) solid binding maker: from 10 to 80%, and preferably from 30 to 60% by weight.

In the "bulk" biosensors according to the present invention, the biocatalyst content ranges from 1 to 30% by weight, with respect to the weight of the composite transducer. When said biocatalyst is an enzyme requiring the presence of a co-factor, the quantity of co-factor ranges from 0.5 to 30%, and preferably from 3 to 10% by weight of the composite transducer.

The biosensor of the present invention can be prepared according to different shapes and geometries. FIG. 1 shows a cylindrical biosensor; however, it can be prepared even in other geometrical shapes, such as in the form of parallelepipedon, sphere, plate, film, screen printed layer and so on.

The composite transducer can be prepared according to the following steps:
1) said electro-conducting material is mixed with said chemical mediator;
2) the thus obtained mixture is optionally mixed with said substance capable of sorption of the chemical mediator;
3) the mixture obtained in step (1) or (2) is suitably mixed with said solid binding maker;
4) the mixture obtained in stage (3) is introduced and optionally pressed in a compact form, thus obtaining the composite transducer. Said composite transducer can be smoothed at the base, for example on a sheet of common paper.

In step (3), the admixing of the solid binding maker has to be carried out by preferably mixing according to one of the following procedures:
vigorous mechanical mixing of all solid components;
mixing in the presence of a suitable solvent which is then evaporated, preferably chloroform or ethanol;
mixing the mixture obtained in step (1) or (2) with the solid binding maker in melted state.

For the preparation of a preferred embodiment of the biosensor of the invention, a biocatalytic layer can be applied onto the base surface of said composite transducer, as shown in FIG. 1A.

Figure 1B:
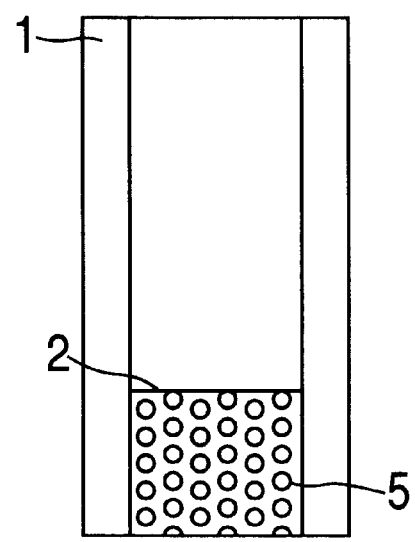
FIG. 1B, said biocatalyst 5 is incorporated into the bulk of the transducer 2.

Alternatively, according to another embodiment of the biosensor of the invention, the biocatalyst can be directly incorporated in the body of the composite transducer, as shown in FIG. 1B, by its admixing in step (3), thus obtaining a "bulk" biosensor.

Finally, the biosensors of the invention can be covered by a suitable membrane, as described above.

The biosensors according to the present invention show high specificity and sensitivity, and can be advantageously used in human and veterinary diagnostics, in industrial processes, in the quality control of food, in biotechnology, in the pharmaceutical industry, in the environmental monitoring and so on.

The procedure for the detection and quantification of analytes, in sample solutions or suspensions, comprises applying suitable electrode potential, contacting a biosensor according to the present invention, as described above, with said analytes solutions or suspensions and finally measuring current changes, which are proportional to the concentration of the analyte.

The following examples are reported for illustrative, but not limitative purposes.

EXAMPLE 1

Preparation of a transducer containing monostearoyl glycerol as solid binding maker.

1 g of synthetic graphite powder (Aldrich, Cat. No. 28, 286-3, 1994) was added to a solution containing 62 mg of 1,1'-dimethyl-ferrocene (Aldrich) in 5 ml of chloroform. The mixture was stirred at room temperature until chloroform was completely evaporated. 180 mg of the above mixture were mixed thoroughly with alumina (20 mg, 1 $\mu$m average particle size). Monostearoyl glycerol (200 mg) was added and mixed.

Figure 2:
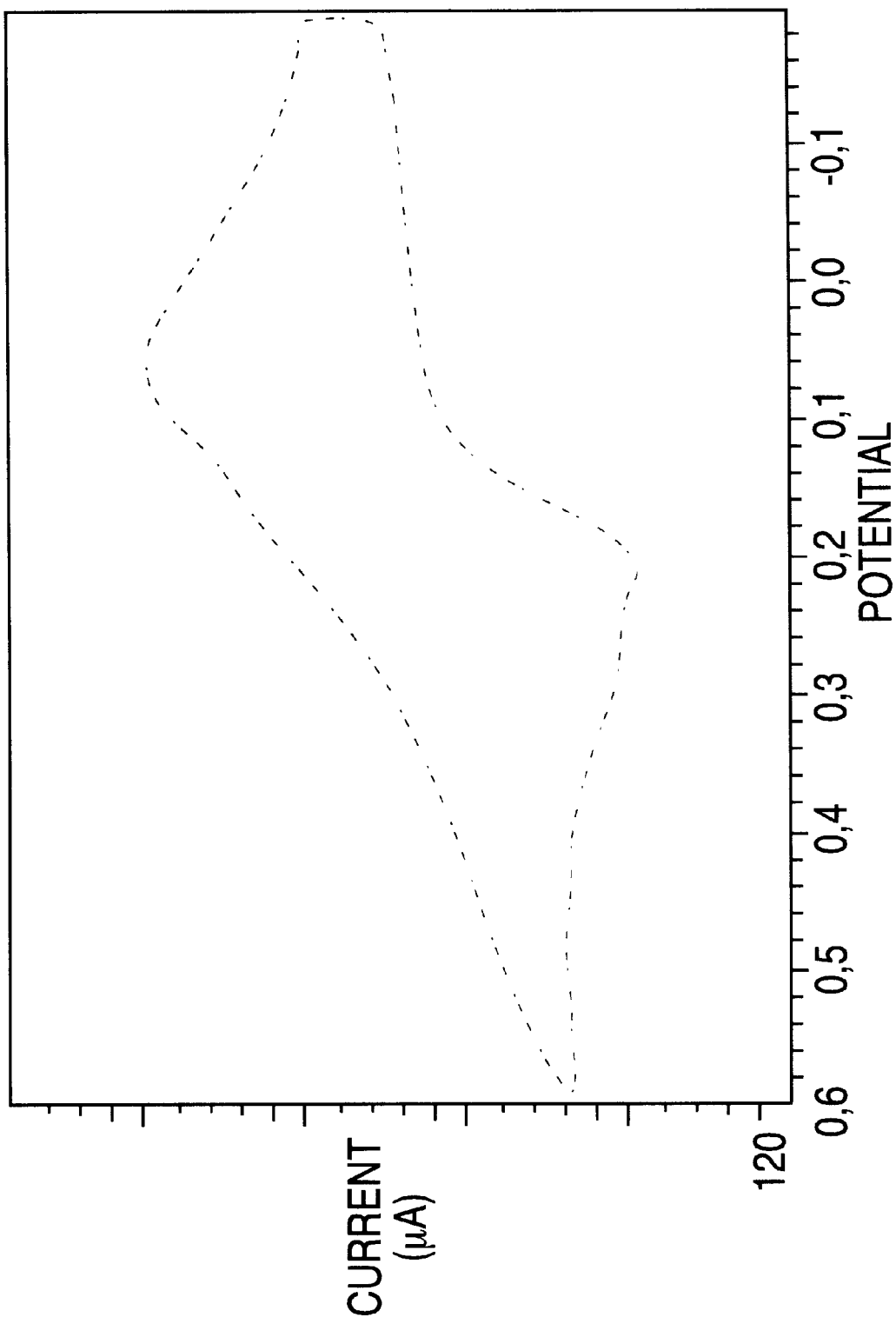
FIGS. 2, 3, and 13 are cyclic voltammograms obtained with transducers prepared respectively in examples 1, 2 and 12.

The thus obtained mixture was introduced in a bottomless glass tube, having an inner diameter of 2 mm, and pressed with a glass rod. The surface of the electrode was smoothed on a sheet of ordinary paper. The electric contact was made through a copper wire. The obtained transducer was tested by cyclic voltammetry under the following conditions: 0.1 M sodium phosphate, pH=6.5, saturated with nitrogen, scan rate 100 mV/s, instrumentation Amel—model 433V, saturated calomel reference electrode (SCE), Pt counter electrode. The cyclic voltammogram is shown in FIG. 2.

EXAMPLE 2

Preparation of a transducer containing monostearoyl glycerol as solid binding maker.

Figure 3:
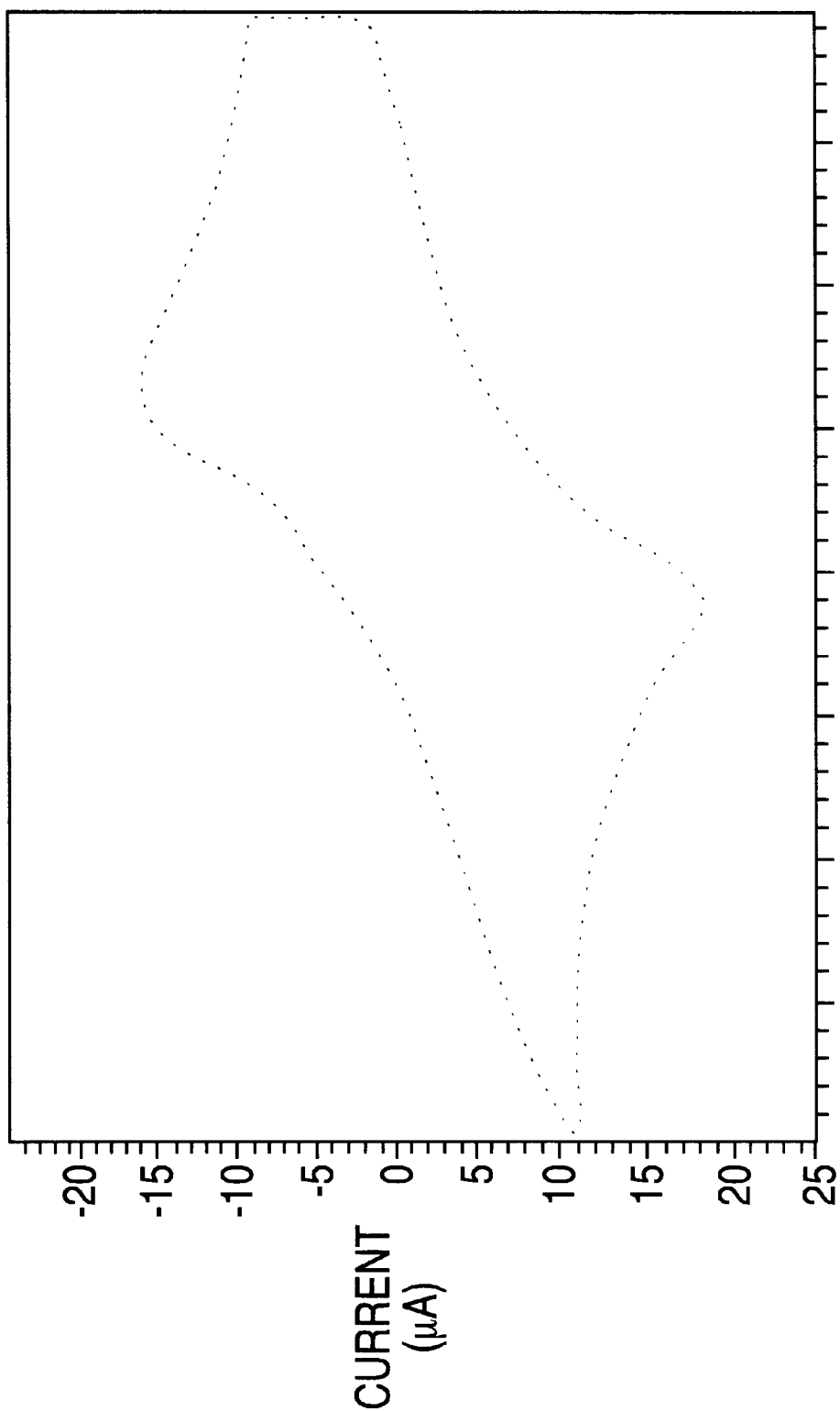

Graphite powder was added to 1,1'-dimethyl-ferrocene, as described in Example 1. The obtained product (200 mg) was thoroughly mixed with Nafion® (100 $\mu$l of 5%, Aldrich, Cat. No. 27,470-4, 1994) and then with monostearoyl glycerol (200 mg). The obtained mixture was introduced in a bottomless glass tube and tested under the conditions described in Example 1. The cyclic voltammogram is shown in FIG. 3.

EXAMPLE 3

Preparation of a "bulk" biosensor for the determination of glucose, containing monostearoyl glycerol as solid binding maker.

Figure 4:
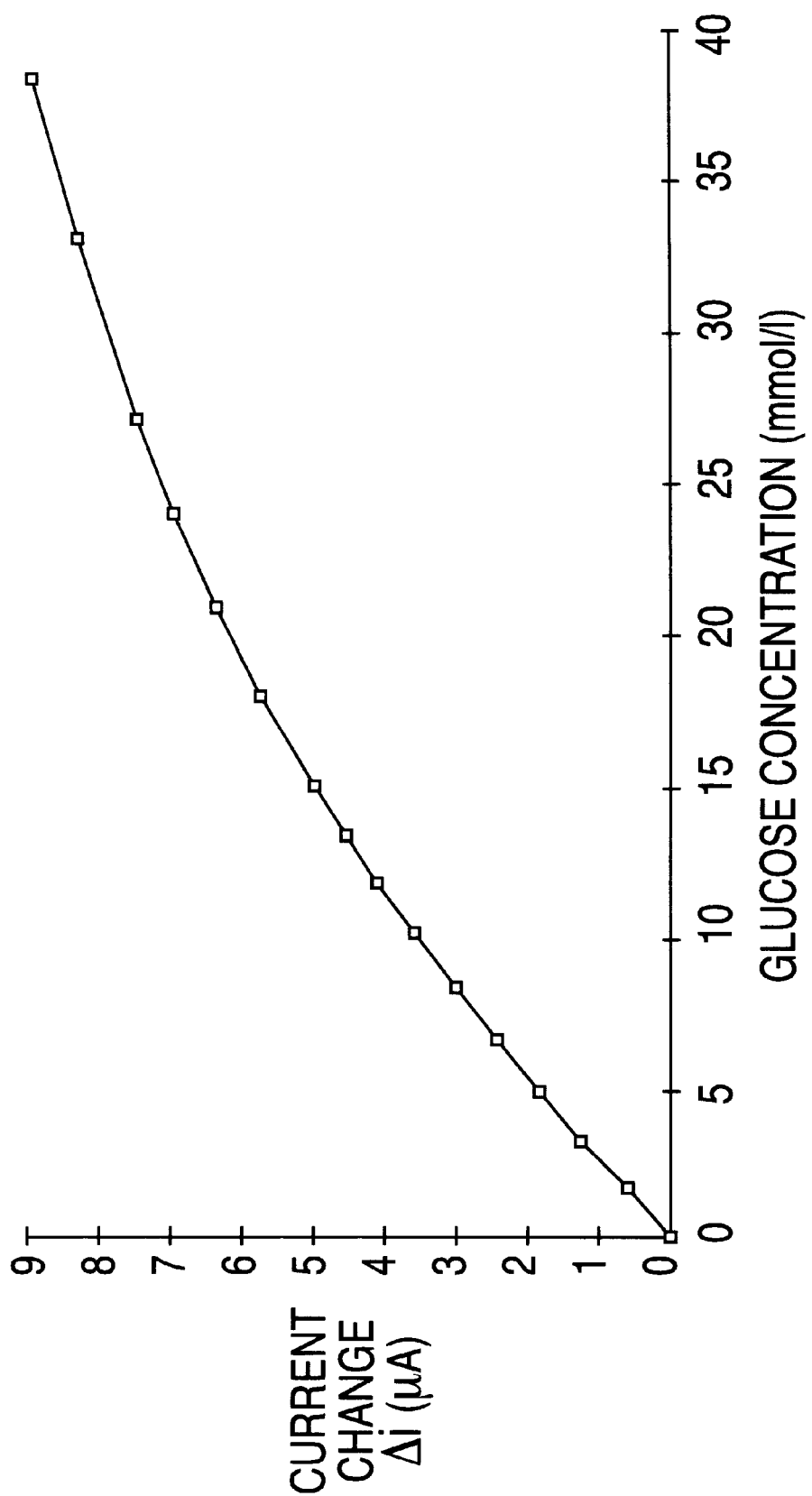
FIG. 4 shows the relationship between current value and glucose concentration with the "bulk" biosensor prepared in example 3.

Graphite powder was added to 1,1'-dimethyl-ferrocene, as described in Example 1. The obtained mixture (200 mg) was thoroughly mixed with Nafion® (100 $\mu$l of 5%, Aldrich, Cat. No. 27,470-4, 1994). The obtained product (190 mg) was thoroughly mixed with glucose oxidase (10 mg, Sigma. Cat. No. G-7016) and then with monostearoyl glycerol (200 mg). The mixture was introduced in a bottomless glass tube, having an inner diameter of 2 mm, pressed with a metal rod and the base surface was smoothed on a sheet of ordinary paper. The thus obtained biosensor was covered with a dialysis membrane (Spectra/Por® MWCO 6,000–8,000) by means of an O-ring. The biosensor was polarized at 250 mV vs. SCE. The response of the biosensor was recorded in a buffer solution (0.1 M sodium phosphate, pH=6.5), under nitrogen stream (to avoid the effect of oxygen), for several glucose concentrations. The relationship between glucose concentration and current change is shown in FIG. 4. The response was linear up to the concentration of 12 mM. The equation for the linear part of the response is I=0,013+0, 364c, where I is the current value [$\mu$A] and c is the glucose concentration in mM, the coefficient of regression r being 0,9997.

Figure 5:
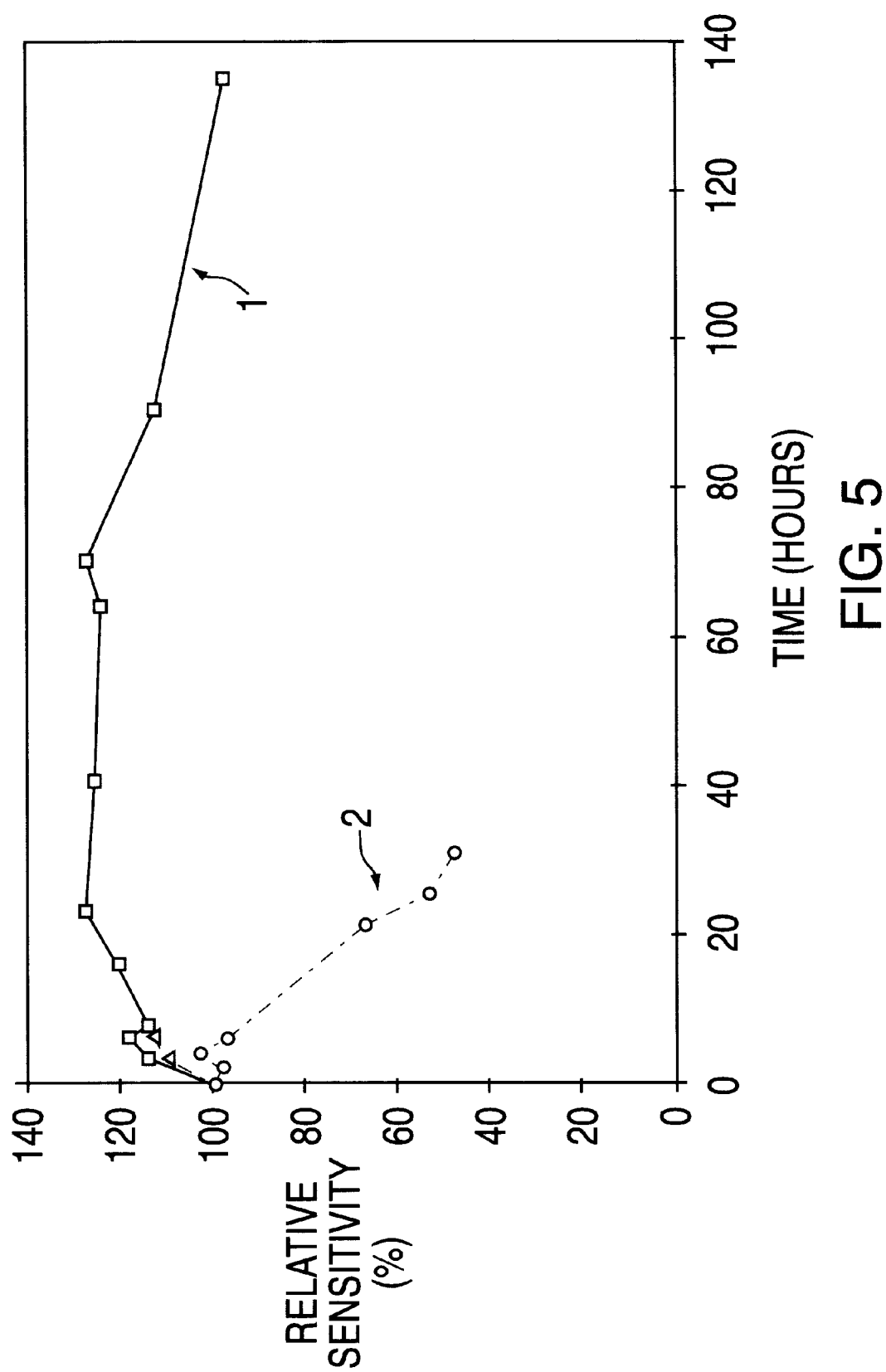
FIG. 5 shows the relationships between polarization time and the relative sensitivity of the biosensor of example 3 (curve 1) and of a similar biosensor, not comprising a solid binding maker, prepared as described in the comparative example 4 (curve 2).

The obtained biosensor underwent also stability tests. It was polarized at potential of 250 mV vs. SCE in a buffered solution of glucose (4 mM), saturated with nitrogen, and the response was recorded after various polarization times. The relationship between relative sensitivity and polarization time is shown in FIG. 5 (curve 1).

COMPARATIVE EXAMPLE 4

Preparation of the "bulk" biosensor of example 3, in the absence of monostearoyl glycerol as solid binding maker.

A biosensor was prepared as described in Example 3, without adding monostearoyl glycerol as solid binding maker. In order to confer consistency to the transducer, ordinary wax was added to the mixture instead of monostearoyl glycerol. The sensor underwent stability tests, as reported in Example 3. FIG. 5 (curve 2) shows that, in the absence of a suitable solid binding maker, the stability of the biosensor is significantly reduced.

EXAMPLE 5

Preparation of a "bulk" biosensor for the determination of glucose, containing cholesteryl oleate as solid binding maker.

Figure 6:
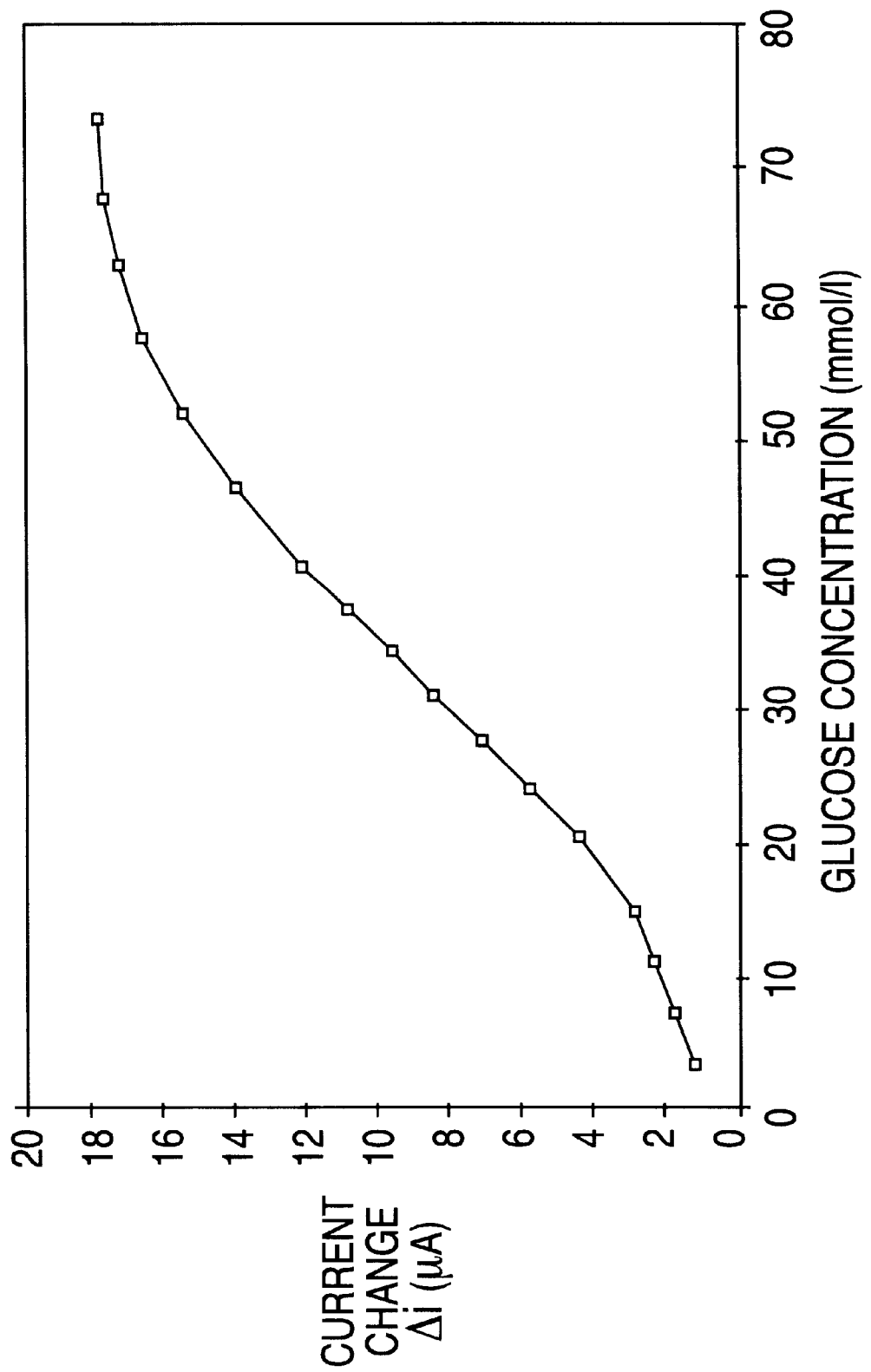
FIGS. 6–8, 10, 14 and 19 show the relationship between current values and glucose concentrations with the biosensors prepared respectively in examples 5–7, 9, 18 and 19.

Graphite powder was added to 1,1'-dimethyl-ferrocene, as described in Example 1. The obtained product (45 mg) was thoroughly mixed with alumina (10 mg), glucose oxidase (4 mg) and cholesteryl oleate (42 mg, Sigma, Cat. No. C-9253, 1994). The obtained mixture was introduced in a bottomless glass tube, having an inner diameter of 2 mm, and pressed with a metal bar. The base surface was then smoothed on a sheet of ordinary paper. The thus obtained biosensor was covered with a dialysis membrane (Spectra/Por®, MWCO 6,000–8,000) by means of an O-ring. The electrode was polarized at 300 mV vs. SCE. The response of the electrode was recorded in a buffer solution (0.1 M sodium phosphate, pH=6.5), under nitrogen stream (to avoid the effect of oxygen), at several glucose concentrations. The relationship between glucose concentration and current change is shown in FIG. 6.

EXAMPLE 6

Preparation of a "bulk" biosensor for the determination of glucose, containing lecithin as solid binding maker.

Figure 7:
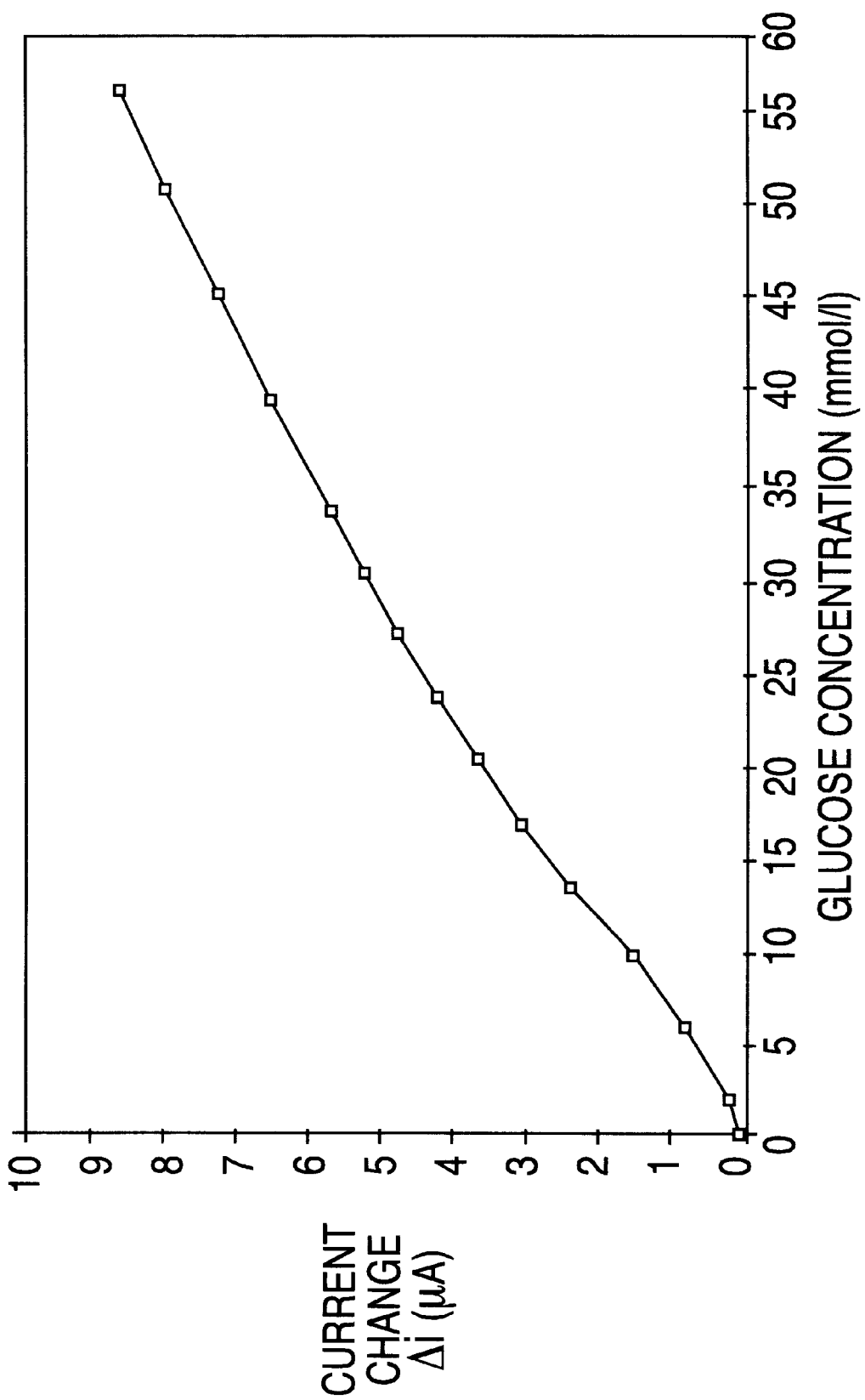

Graphite powder was added to 1,1'-dimethyl-ferrocene, as described in Example 1. The obtained product (45 mg) was thoroughly mixed with alumina (10 mg), glucose oxidase (4 mg) and lecithin (30 mg, Fluka, Cat. No. 61755, 1993–1994). The obtained mixture was introduced in a glass tube, pressed and smoothed, and the obtained biosensor was covered with a dialysis membrane, as described above. The obtained electrode was polarized at 300 mV vs. SCE. The response of the biosensor was recorded in a buffer solution (0.1 M sodium phosphate, pH=6.5), under nitrogen stream (to avoid the effect of oxygen), at several glucose concentrations. The relationship between glucose concentration and current change is shown in FIG. 7.

EXAMPLE 7

Preparation of a "bulk" biosensor for the determination of glucose, containing monostearoyl glycerol as solid binding maker.

Figure 8:
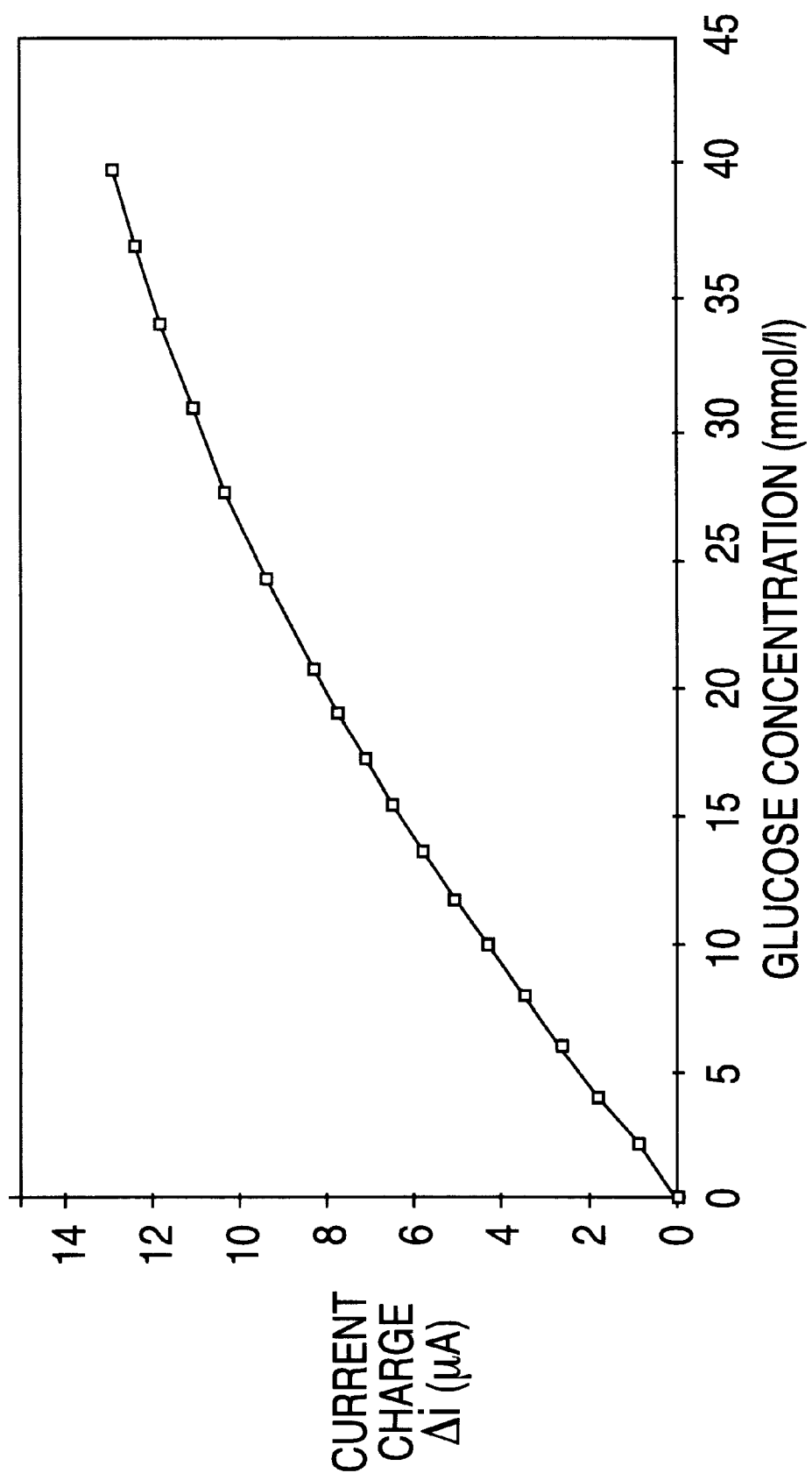

1 g of graphite powder was added to a solution of 62 mg of tetrathiafulvalene (Aldrich, Cat. No. 18,318-0, 1995) in 5 ml of chloroform, as described in example 1. 45 mg of the obtained product were thoroughly mixed with alumina (10 mg), glucose oxidase (4 mg), and monostearoyl glycerol (45 mg). The obtained mixture was introduced in a glass tube, pressed and smoothed, and the obtained biosensor was covered with a dialysis membrane, as described above. The obtained electrode was polarized at 300 mV vs. SCE. The response of the electrode was recorded in a buffer solution (0.1 M sodium phosphate, pH=6.5), under nitrogen stream (to avoid the oxygen influence), at several glucose concentrations. The relationship between glucose concentration and current change is shown in FIG. 8.

EXAMPLE 8

Preparation of a "bulk" biosensor for the determination of ethanol, containing monostearoyl glycerol as solid binding maker.

1. Preparation of *Gluconobacter oxydans* cells

Cells of *Gluconobacter oxydans* CCM 1783 were grown in a culture medium (100 g of glycerol, 5 g of yeast extract per 1 l, tap water), at 30° C. In the late exponential phase ($OD_{650}$=0.6), the suspension was centrifuged (5 min at 4,500 rpm), washed three times with a solution of NaCl (10 g/l) and dried under reduced pressure.

2. Preparation of biosensor

Graphite powder was added to 1,1'-dimethyl-ferrocene, as described in Example 1. The obtained product (200 mg) was thoroughly mixed with Nafion® (100 μl of 5%, Aldrich, Cat. No. 27,470-4, 1994). The mixture (120 mg) was thoroughly mixed with 9 mg of the dried biomass of *Gluconobacter oxydans* and then with monostearoyl glycerol (120 mg).

Figure 9:
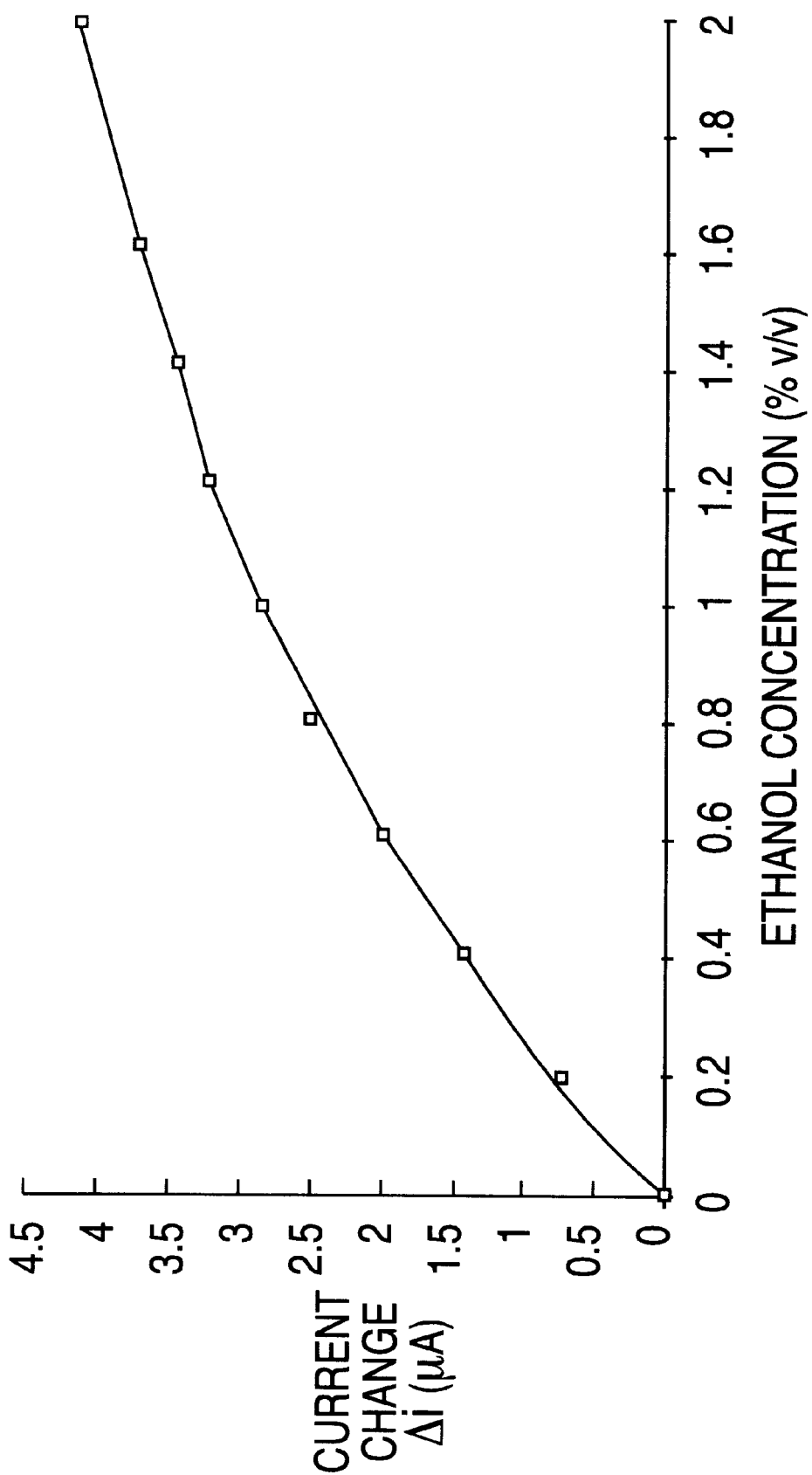
FIGS. 9, 11, 12 and 16–18 show the relationship between current values and ethanol concentrations with the biosensors prepared respectively in examples 8, 10, 11 and 15–17.

The obtained mixture was introduced in a glass tube, pressed and smoothed, and the obtained biosensor was covered with a dialysis membrane, as described above. The biosensor was polarized at 250 mV vs. SCE. The response of the biosensor was recorded in a buffer solution (0.1 M sodium phosphate, pH=6.5), under nitrogen stream (to avoid the effect of oxigen), at several ethanol concentrations. The relationship between ethanol concentration and current change is shown in FIG. 9.

EXAMPLE 9

Preparation of a biosensor for the determination of glucose, based on a layer of glucose oxidase and containing monostearoyl glycerol as solid binding maker.

Figure 10:
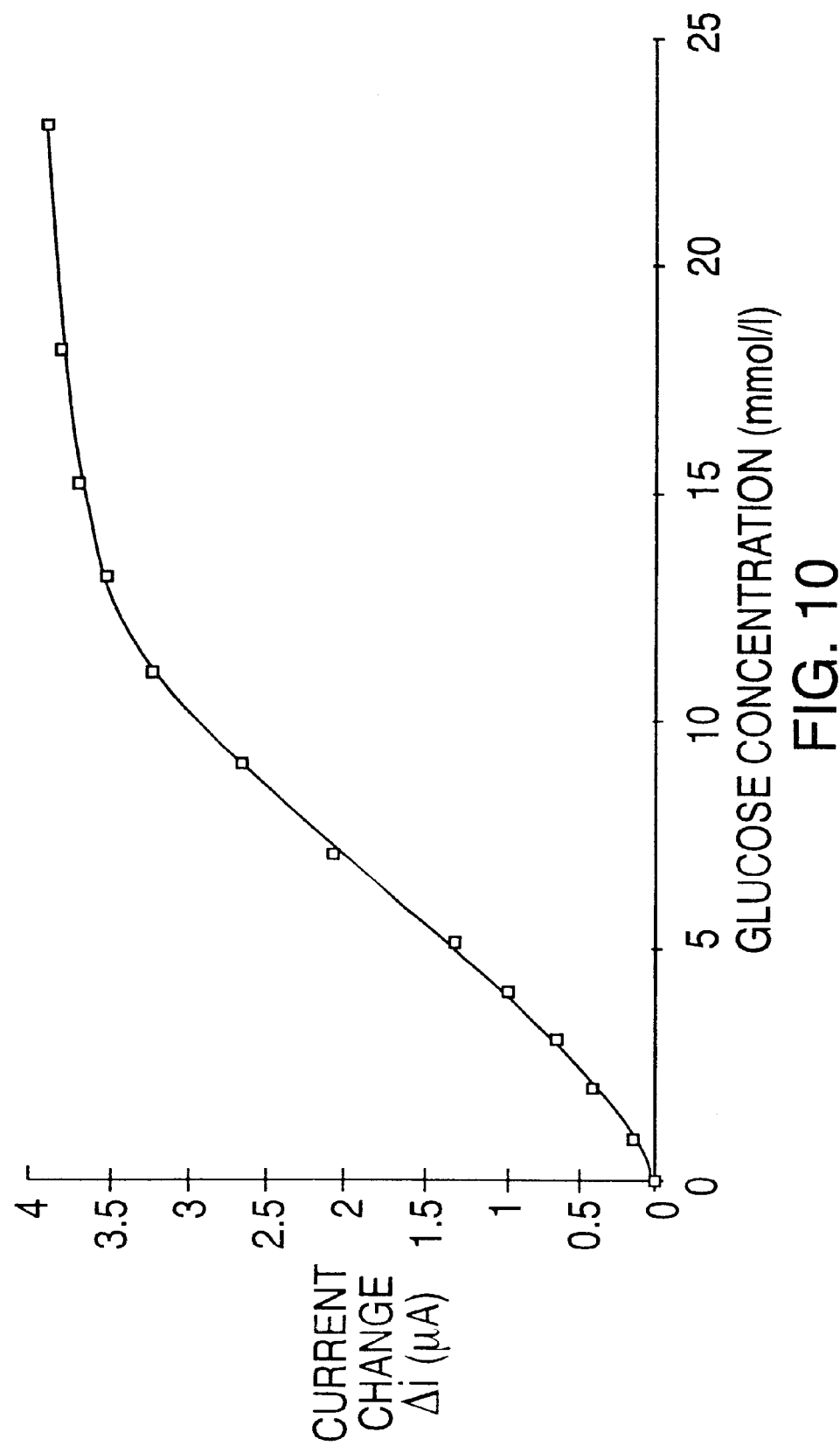

A transducer was prepared as described in Example 2. Glucose oxidase (2 μl, 100 mg/ml) was then applied on the base surface of the transducer. After drying, the obtained biosensor was covered with a dialysis membrane (Spectra/Por® MWCO 6,000–8,000), by means of an O-ring. The obtained biosensor was polarized at 250 mV vs. SCE. The response was recorded in a buffer solution (0.1 M sodium phosphate, pH=6.5), under nitrogen stream (to avoid the effect of oxygen), at several glucose concentrations. The relationship between glucose concentration and current change is shown in FIG. 10.

EXAMPLE 10

Preparation of a biosensor for the determination of ethanol, based on a layer of cells of *Gluconobacter oxydans* and containing monosteroyl glycerol as solid binding maker.

1. Preparation of *Gluconobacter oxydans* cells

Cells of *Gluconobacter oxydans* CCM 1783 were grown under the conditions described in Example 8. In the late exponential phase ($OD_{650}$=0.6), a part of the suspension (25 ml) was centrifuged (5 min at 4,500 rpm), washed three times with a solution of NaCl (10 g/l) and finally resuspended in the same NaCl solution (1 ml).

2. Preparation of biosensor

Figure 11:
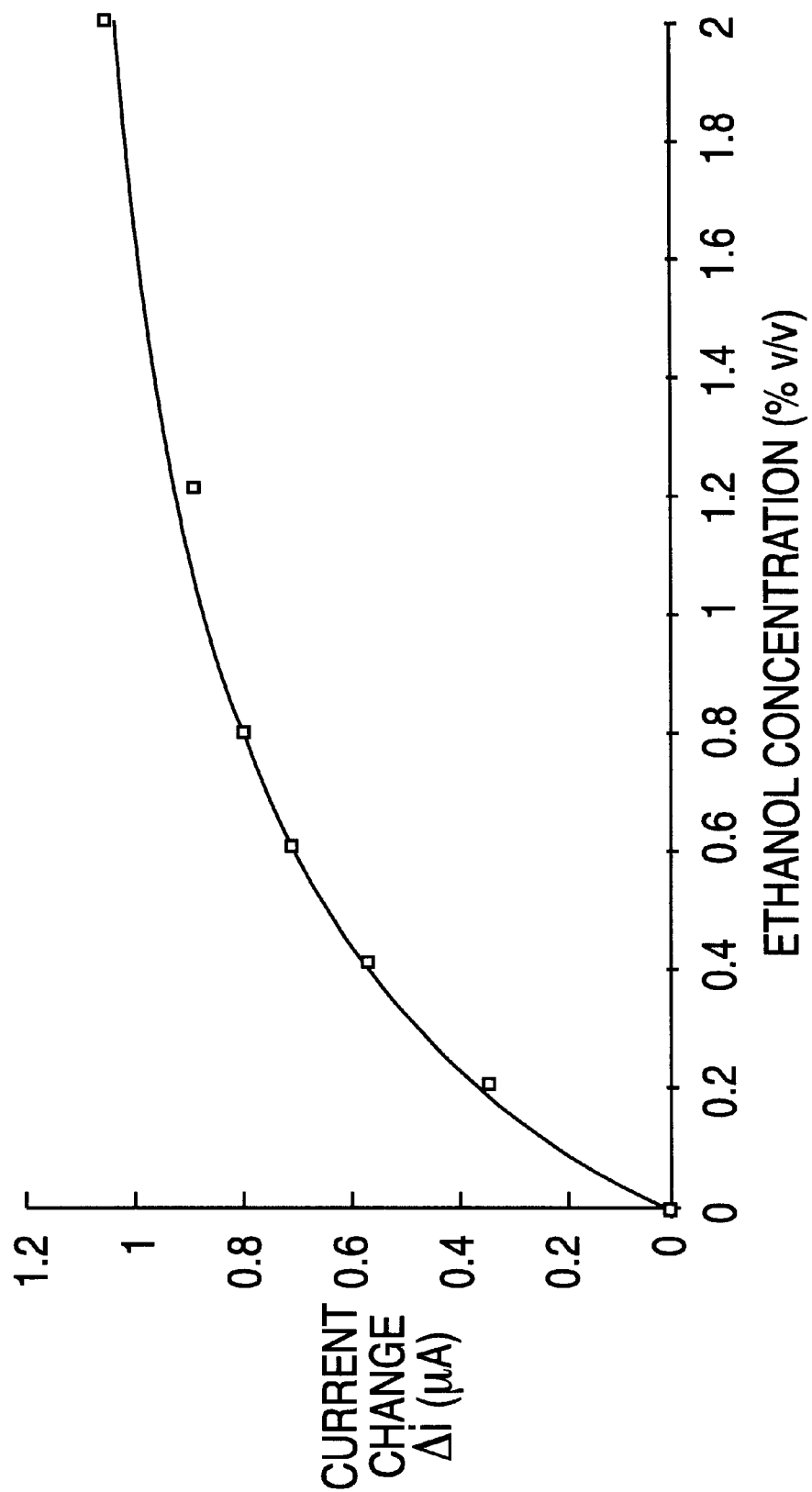

A disc of filter paper was put onto a Petri dish and the paper was soaked with NaCl solution. A disc of membrane for microfiltration (Millipore, HA 45 μm porosity, 5 mm diameter) was put onto said soaked filter paper and the suspension of *Gluconobacter oxydans* (10 μl) was applied onto the membrane. After suction of the liquid, the disc was put onto the base surface of the transducer, prepared as reported in Example 2, and fixed by means of a nylon net and of an O-ring. The biosensor was polarized at 250 mV vs. SCE. The response of the biosensor was recorded in a buffer solution (0.1 M sodium phosphate, pH=6.5), under nitrogen stream (to avoid the effect of oxygen), at several ethanol concentrations. The relationship between ethanol concentration and current change is shown in FIG. 11.

EXAMPLE 11

Preparation of a "bulk" biosensor for the determination of ethanol, containing monostearoyl glycerol as solid bindig maker.

Figure 12:
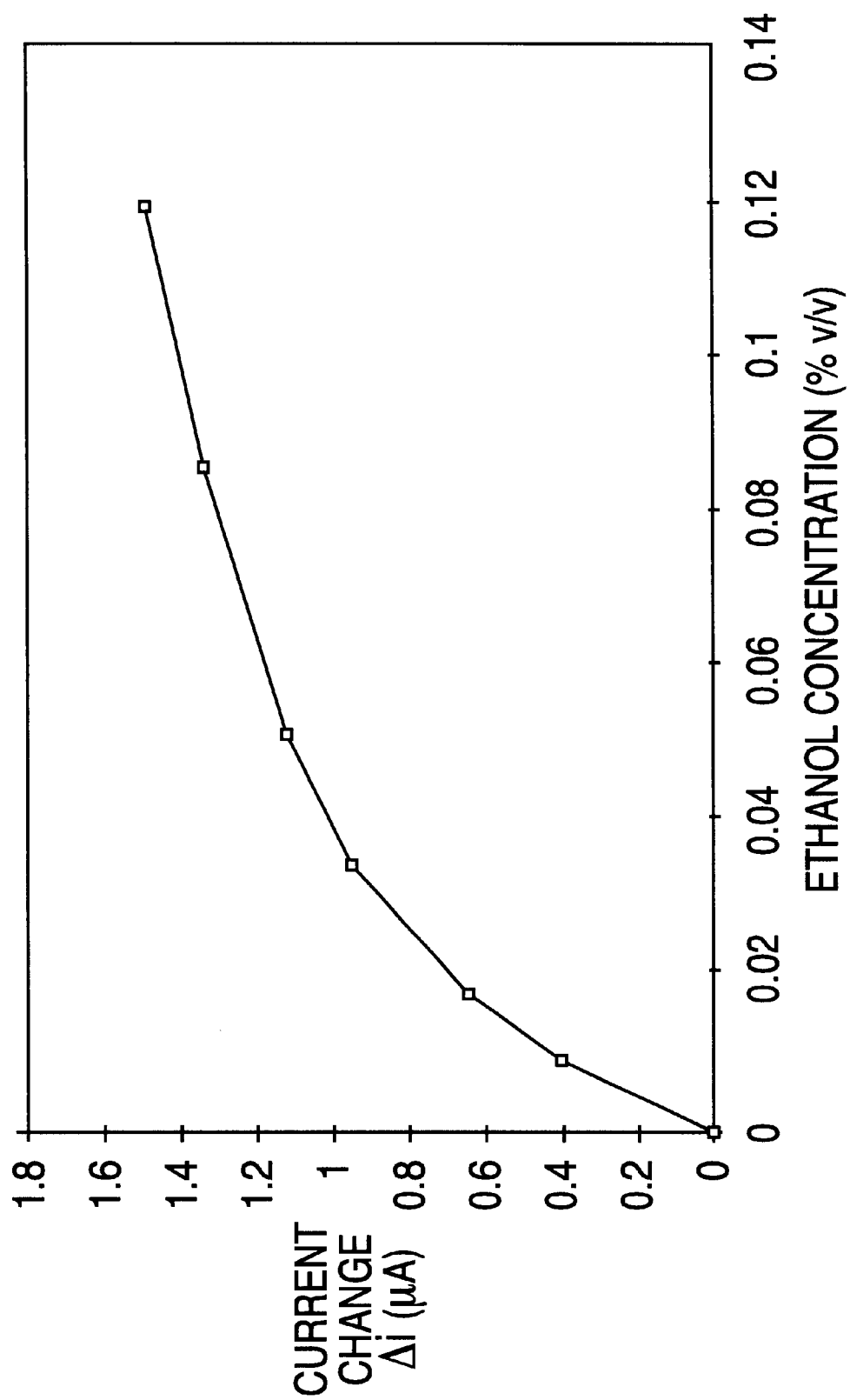

Graphite powder was added to 1,1'-dimethyl-ferrocene, as described in Example 1. The obtained mixture (40 mg) was thoroughly mixed with alumina (10 mg), NAD (5 mg, Fluka, Cat. No 43407, 1995–1996) and alcohol dehydrogenase (3 mg, Sigma Cat. No A-7011, 1995). The thus prepared product was mixed with monostearoyl glycerol (42 mg). The mixture was introduced in a glass tube, preessed and smoothed, and the obtained biosensor was covered with a dialysis membrane, as described above. The obtained biosensor was polarized at 250 mV vs. SCE. The response of the biosensor was recorded in a buffer solution (0.5 M TRIS-HCl buffer, pH=8.8), at several ethanol concentrations. The relationship between ethanol concentration and current change is shown in FIG. 12.

EXAMPLE 12

Preparation of a transducer containing cholesteryl myristate as solid binding maker.

Figure 13:
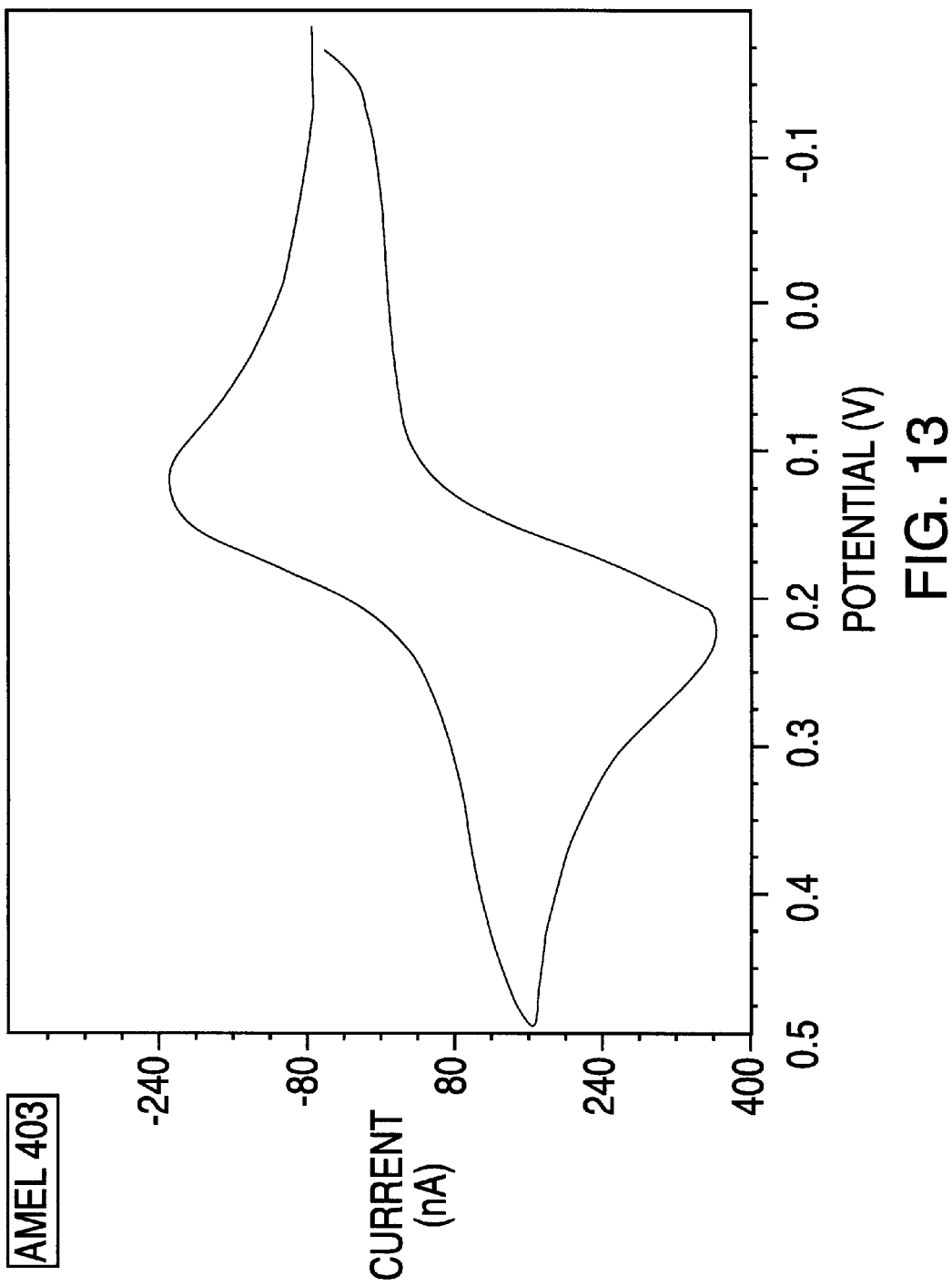

1 g of graphite powder was added to 62 mg of ferrocene, as described in Example 1. Cholesteryl myristate (200 mg, Sigma, Cat.No. C-5076, 1994) was melted in a porcelain dish, immersed in an oil bath heated to 85° C. The above modified graphite (150 mg) was added into the melted mass and thoroughly mixed. A PVC tip (inner diameter 2 mm, outer diameter 5 mm, length 20 mm) was used as a holder of electrode. Into said tip, a brass stick (diameter 2 mm, length 70 mm) was inserted to create cylindrical space (thickness 2–3 mm). The space was filled with the melted mass. The electrode was left to cool to room temperature and the excess of the material was cut out on a sand paper (type P 1000). The surface was then smoothed on a sheet of common paper. The transducer was tested by cyclic voltammetry, under the conditions described in Example 1. The voltammogram is shown in FIG. 13.

EXAMPLE 13

Preparation of a biosensor for the determination of glucose, based on a layer of glucose oxidase and containing cholesteryl myristate as solid bindig maker.

Figure 14:
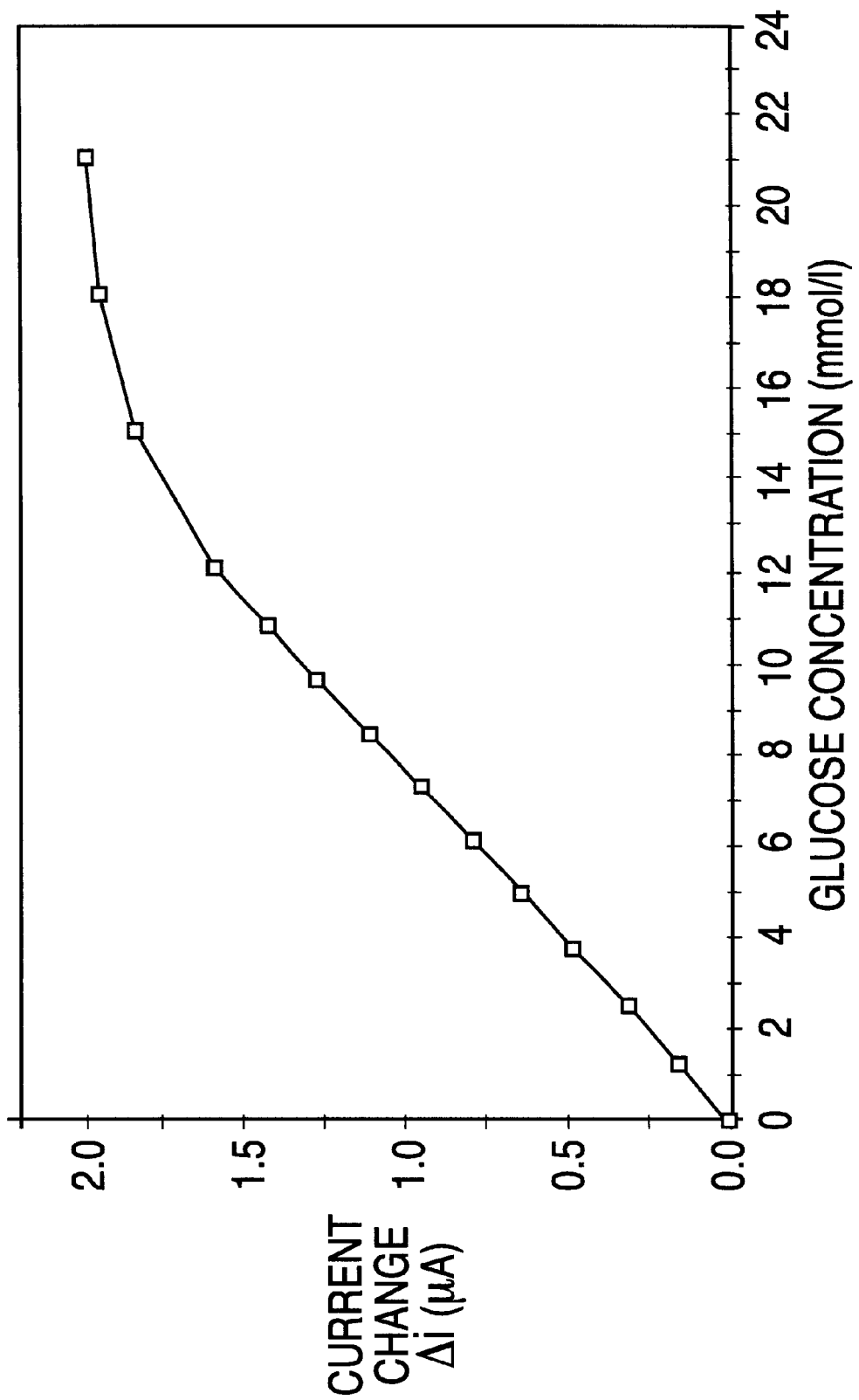

A solution of glucose oxidase (2 μl, 10 mg/ml) was put and spread over the surface of a transducer, prepared according to Example 12. After drying, the electrode was covered by a dialysis membrane (Spectra/Por®, MWCO 6,000–8,000), by means of an O-ring. The electrode was polarized at 300 mV vs. SCE. The response of the electrode was recorded in a buffer solution (0.2 M sodium phosphate buffer, pH=8), for various glucose concentrations. The relationship between glucose concentration and current change is shown in FIG. 14.

EXAMPLE 14

Preparation of a biosensor for the determination of fructose, based on a layer of fructose dehydrogenase and containing cholesteryl myristate as solid bindig maker.

Figure 15:
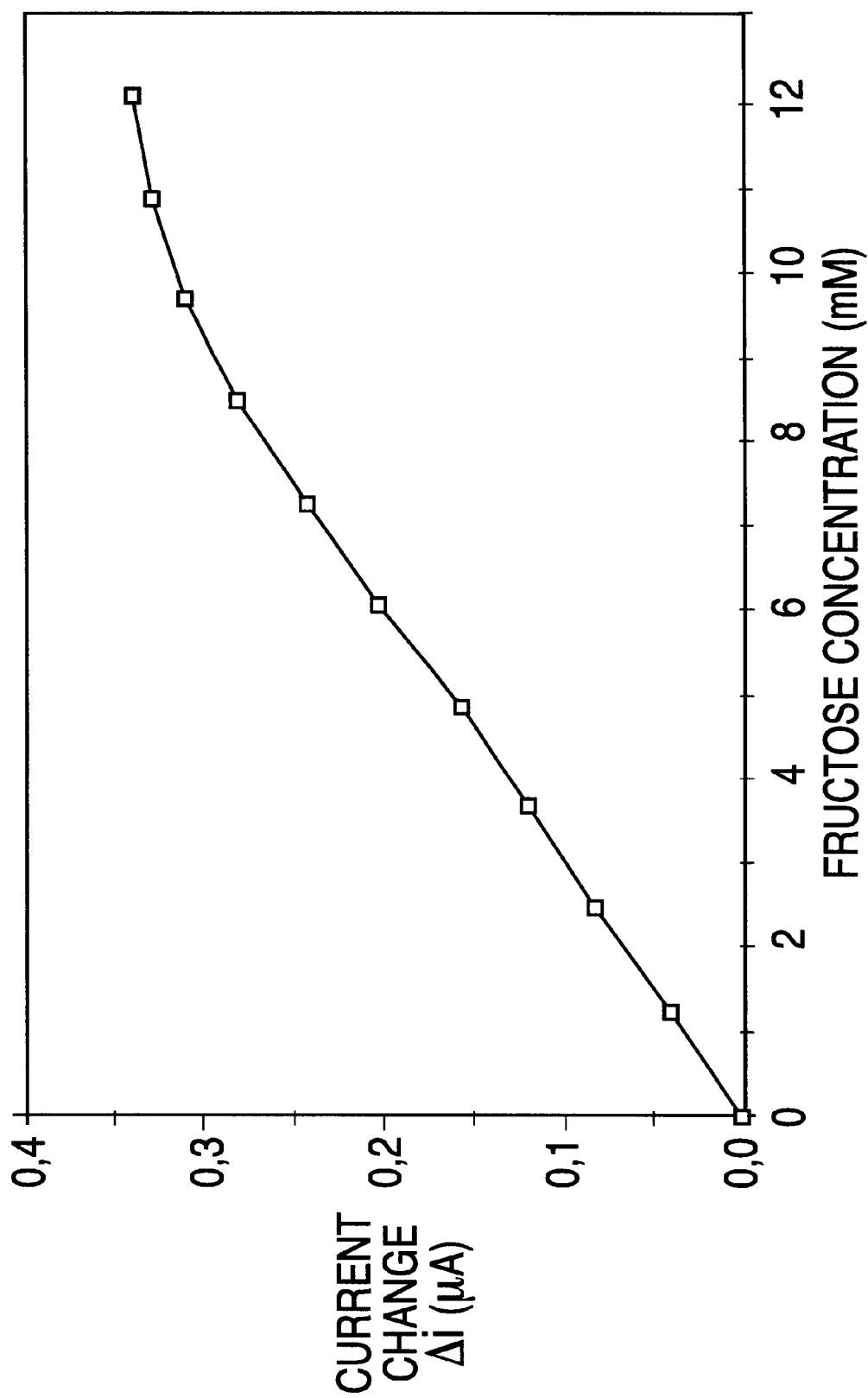
FIG. 15 shows the relationship between current value and fructose concentration with the biosensor prepared in example 14.

A solution of fructose dehydrogenase (1 μl, 18 mg/ml, Sigma, Cat.No. F-4892, 1995) was put and spread over the surface of a transducer, prepared according to Example 12. After drying, the electrode was covered by a dialysis membrane, as described above. The electrode was polarized at 300 mV vs. SCE. The response of the electrode was recorded in a buffer solution (0.2 M sodium phosphate buffer, pH=5.8), for various fructose concentrations. The relationship between fructose concentration and current change is shown in FIG. 15.

EXAMPLE 15

Preparation of a biosensor for the determination of ethanol, containing cholesteryl myristate as solid bindig maker, supplementing the tested solutions with a chemical mediator.

Figure 16:
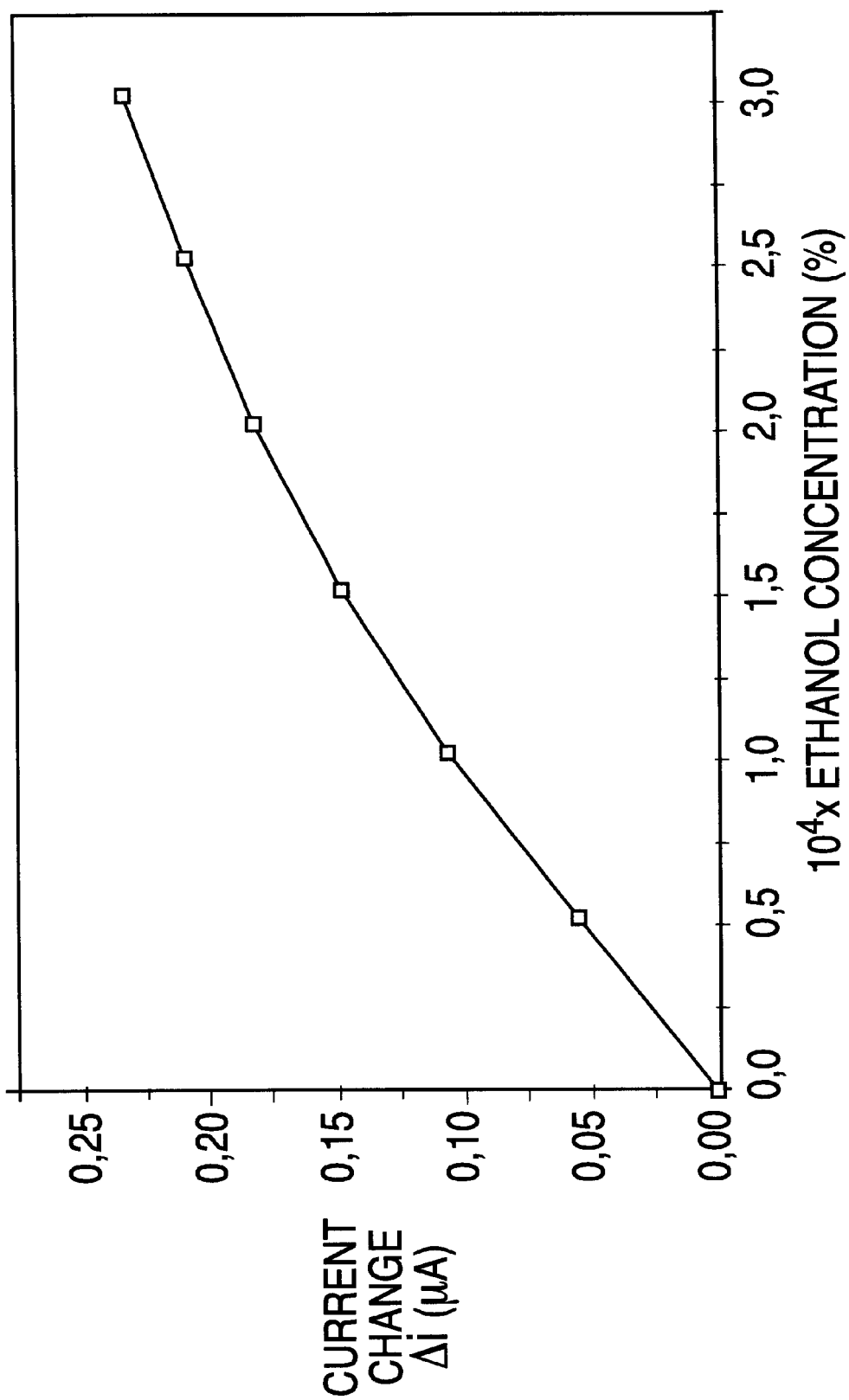

NAD (8 mg) was dissolved in distilled water (1 ml) and graphite powder (74 mg) was added. The obtained suspension was stirred for 30 minutes at room temperature. Water was then evaporated, under reduced pressure. The obtained product was added into melted cholesteryl myristate (120 mg), thoroughly mixed and then introduced into a PVC tip, under the conditions indicated in Example 12. The obtained electrode was left to cool to room temperature and the excess of the material was cut out on a sand paper (type P 1000). The surface was then smoothed on a sheet of common paper. A solutions of ADH (1 μl, 5 mg/ml) and diaphorase (1,5 μl, 50 mg/ml, Sigma, Cat.No. D-5540, 1995) were mixed and spread over the surface of the obtained transducer. After drying, the electrode was covered by a dialysis membrane, as described above. The obtained electrode was polarized at 300 mV vs. SCE. The response of the electrode was recorded in a buffer solution (0.5 M TRIS-HCl buffer, pH=8.8), supplemented with 2 mM hexacyanoferrate (III), for various ethanol concentrations. The relationship between ethanol concentration and current change is reported in FIG. 16.

EXAMPLE 16

Preparation of a biosensor for the determination of ethanol, containing cholsteryl myristate as solid bindig maker, supplementing the tested solutions with a chemical mediator.

Figure 17:
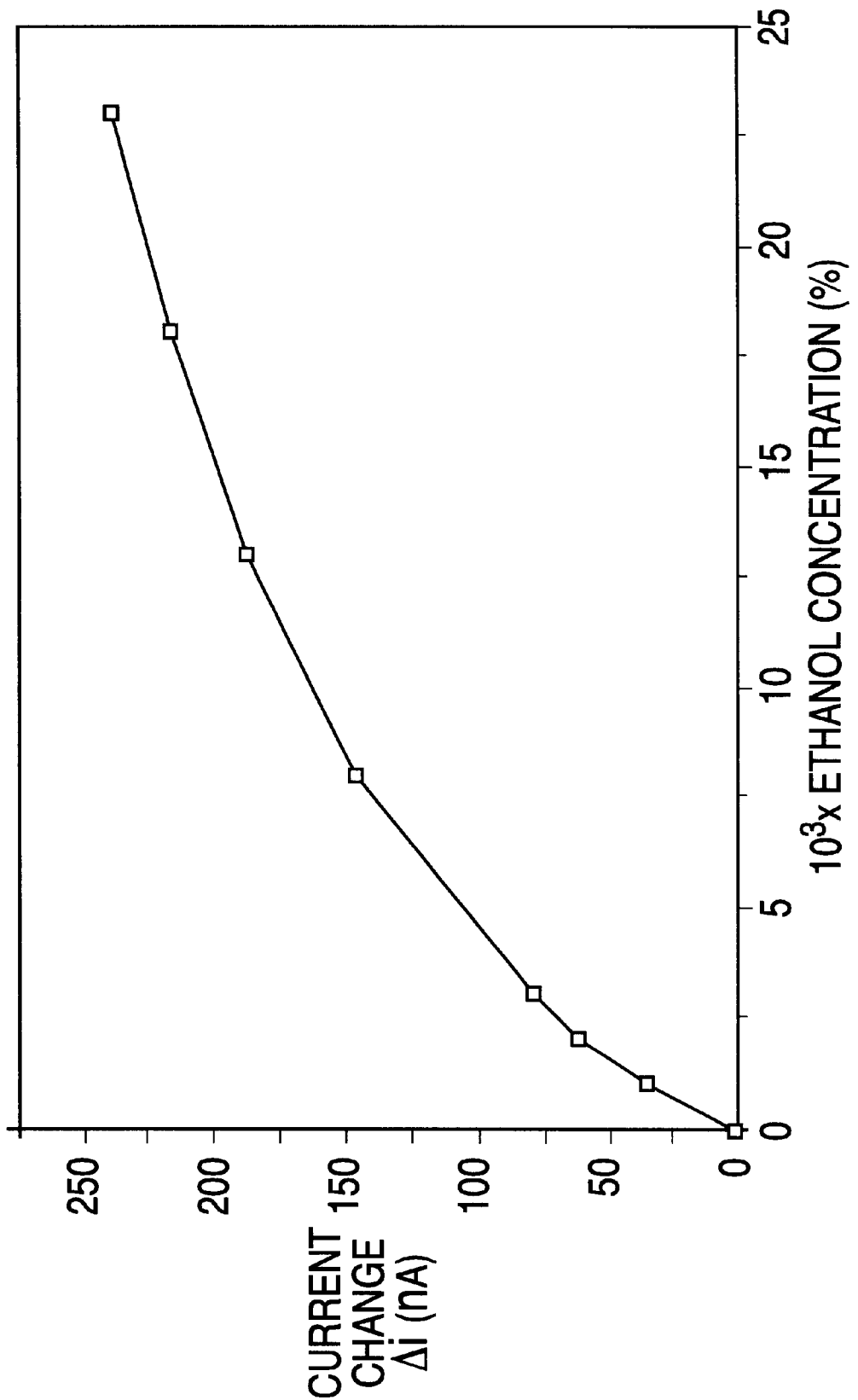

NAD (8 mg), diaphorase (6 mg) and ADH (2 mg) were dissolved in distilled water (1 ml) and graphite powder (70 mg) was added. The suspension was stirred for 30 minutes at room temperature. Water was then evaporated, under reduced pressure. The obtained product was added into melted cholesteryl myristate (125 mg), thoroughly mixed and then introduced into a PVC tip, under the conditions reported in Example 12. The obtained electrode was left to cool to room temperature and the excess of the material was cut out on a sand paper (type P 1000). The surface was then smoothed on a sheet of common paper and covered with a dialysis membrane, as desribed above. The electrode was polarized at 300 mV vs. SCE. The response of the electrode was recorded in a buffer solution (0.5 M TRIS-HCl buffer, pH=8.8) supplemented with 2 mM hexacyanoferrate (III), for various ethanol concentrations. The relationship between ethanol concentration and current change is shown in FIG. 17.

EXAMPLE 17

Preparation of a "bulk" biosensor for the determination of ethanol, containing cholesteryl myristate as solid bindig maker, supplementing the tested solutions with a chemical mediator.

Figure 18:
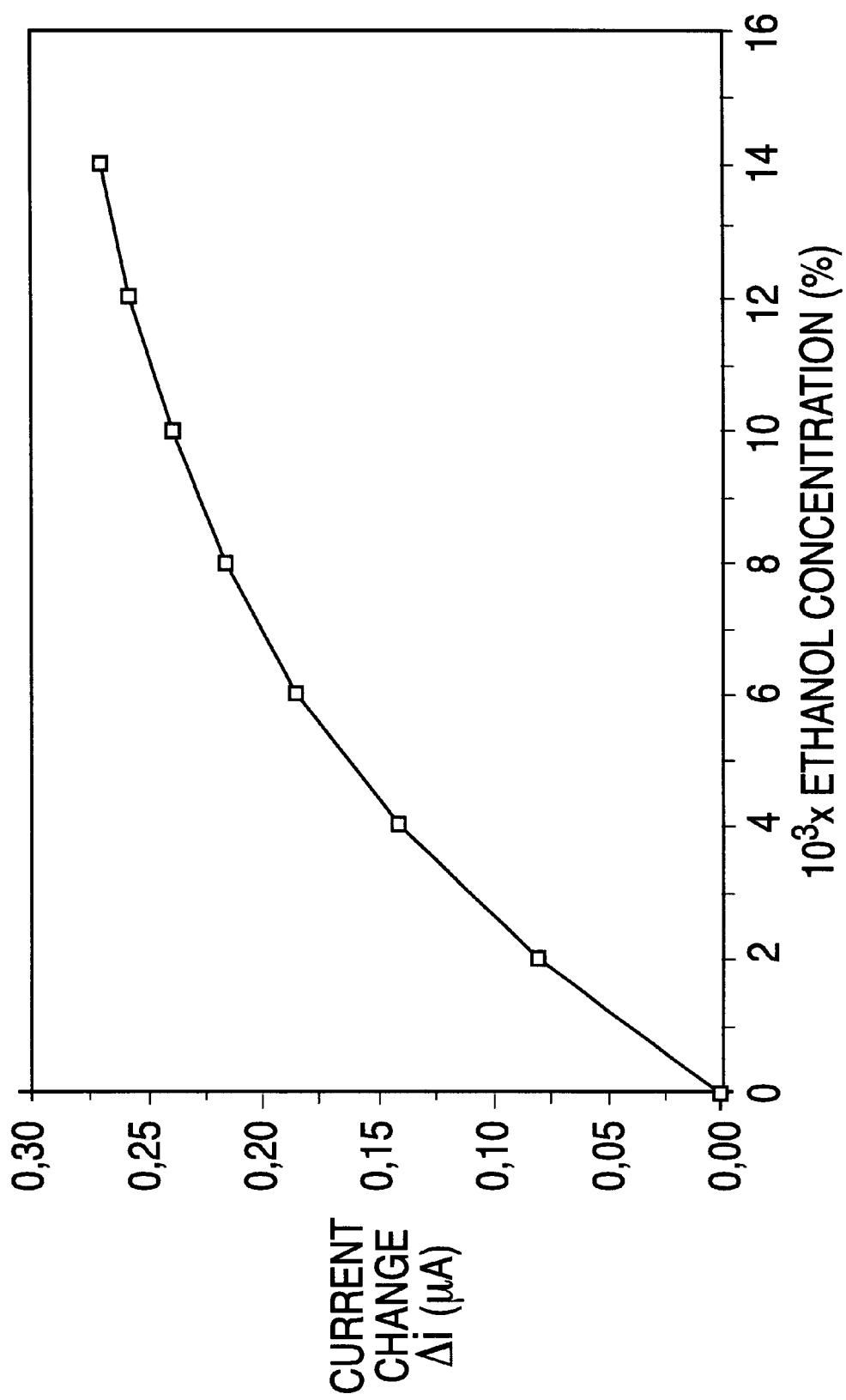

NAD (5 mg), diaphorase (4 mg), ADH (2 mg) and graphite powder (60 mg) were thoroughly mixed in a mortar; to the obtained mixture, cholesteryl myristate (95 mg) was added and mixed. Chloroform (80 μl) was added and the mixture was vigorously stirred until the solvent was evaporated. The final product was introduced into a PVC tube, having an inner diameter of 2 mm, and pressed with a metal rod. The surface was then smoothed on a sheet of common paper and covered with a dialysis membrane, as desribed above. The obtained electrode was polarized at 300 mV vs. SCE. The response of the electrode was recorded in a buffer solution (0.5 M TRIS-HCl buffer, pH=8.8), supplemented with 2 mM hexacyanoferrate (III), for various ethanol concentrations. The relationship between ethanol concentration and current change is shown in FIG. 18.

EXAMPLE 18

Preparation of a "bulk" biosensor for the determination of glucose, containing hexadecanone as solid binding maker.

Figure 19:
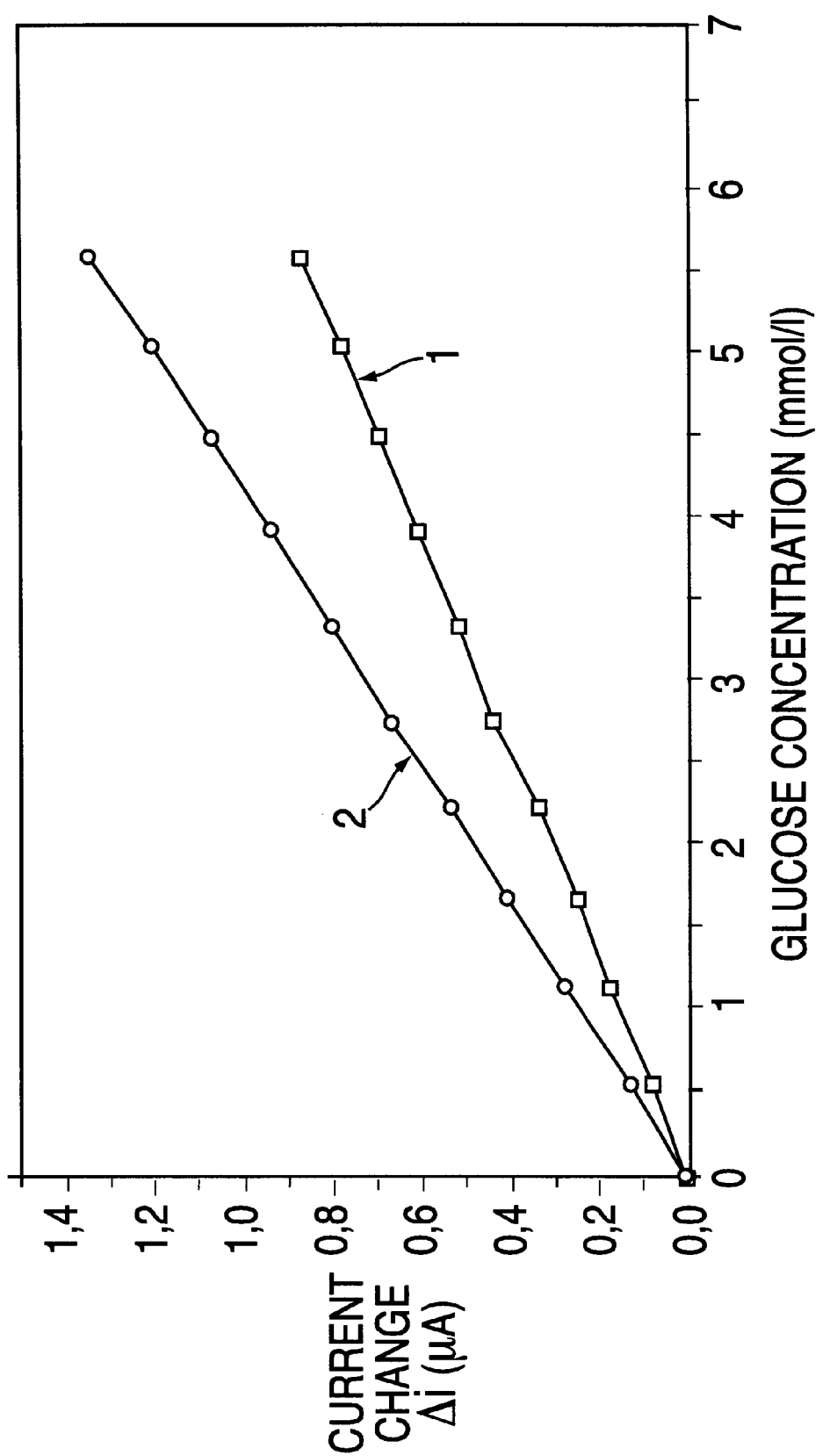

1 g of graphite powder was added to 62 mg of ferrocene, as described in Example 1. 450 mg of the obtained product were thoroughly mixed with a solution of glucose oxidase (50 mg of glucose oxidase in 0.5 ml of water) and water was evaporated under reduced pressure. 53 mg of the mixture was furtherly mixed with melted hexadecanone (70 mg), at the temperature of 50° C., and the obtained mixture was introduced into a PVC tip, cooled, smoothed and finally covered with a dialysis membrane, as described in example 12. The obtained electrode was polarized at 300 mV vs. SCE. The response of the electrode was recorded in a buffer solution (0.2 M sodium phosphate, pH=8), at several glucose concentrations. The relationship between glucose concentration and current change is shown in FIG. 19 (curve 1).

EXAMPLE 19

Preparation of a "bulk" biosensor for the determination of glucose, containing eicosane as solid binding maker.

A biosensor for the determination of glucose was prepared as described in example 18, with the exception of using eicosane as solid binding maker instead of hexadecanone. The obtained electrode was polarized at 300 mV vs. SCE. The response of the electrode was recorded in a buffer solution (0.2 M sodium phosphate, pH=8), at several glucose concentrations. The relationship between glucose concentration and current change is shown in FIG. 19 (curve 2).

What is claimed is:

1. An electrochemical biosensor comprising:
   a) an electro-conducting material, in the form of powder or grains;
   b) a chemical mediator;
   c) a substance absorbing said chemical mediator; and
   d) one solid binding maker, selected from the group consisting of:
      linear or branched, saturated or unsaturated hydrocarbons, containing from 12 to 60 carbon atoms optionally substituted with at least a group selected from —OH, —SH, —NH$_2$, —CO—. —CHO, —SO$_3$H, —COOH, —OR$_1$, —SR$_1$, —NR$_1$R$_2$, and —COOR$_1$, wherein R$_1$ and R$_2$ are independently hydrocarbon groups, C$_1$–C$_{30}$, optionally containing one or more heteroatoms;
      esters of fatty acid or a mixture of fatty acids with glycerol; and
      esters of a fatty acid or a mixture of fatty acids with cholesterol, said solid binding maker having a melting point comprised between 35° C. and 90° C. and said elements a)–d) constituting a composite transducer, and a biocatalyst which is a redox enzyme, and wherein said biocatalyst is either incorporated in bulk into said composite transducer or it is applied in the form of a layer onto the surface of said composite transducer, said electrochemical biosensor being optionally covered by a membrane, and wherein said electrochemical biosensor comprises, with reference to 100 parts by weight of the sum of the components (a)–(d):
   a) from 30 to 60% by weight;
   b) from 1 to 10% by weight;
   c) from 1 to 20% by weight;
   d) from 30 to 60% by weight.

2. The electrochemical biosensor according to claim 1, wherein said biocatalyst is incorporated in bulk into said composite transducer constituted of said components (a)–(d).

3. The electrochemical biosensor according to claim 2, wherein said biocatalyst incorporated in the bulk into said composite transducer is contained in a quantity ranging from 1 to 30% by weight, with reference to the weight of said transducer.

4. The electrochemical biosensor according to claim 1, wherein said biocatalyst is applied in the form of a layer on said composite transducer constituted of said components (a)–(d).

5. The electrochemical biosensor according to claim 1, wherein said electro-conducting material has an average of length, width and depth of a particle of powder or a grain ranging from 0.05 to 200 μm.

6. The electrochemical biosensor according to claim 1, wherein said electro-conducting material is a metal selected from the group consisting of gold, platinum, palladium, iridium and alloys thereof.

7. The electrochemical biosensor according to claim 1, wherein said electro-conducting material is carbon or graphite.

8. The electrochemical biosensor according to claim 1, wherein said chemical mediator is selected from the group consisting of cytochrome, quinone, aminophenol, electronacceptor aromatic compound, eloctrondonor aromatic compound, organic conducting salt, organic dye, metallocene, organometallic complex of Os, Ru and V and inorganic complex of Fe.

9. The electrochemical biosensor according to claim 8, wherein said chemical mediator is selected from the group consisting of tetrathiafulvalene, N-methylphenazinium, tetracyano-p-quinodimethane, tetrathiafulvalene 7,7,8,8,-tetracyano-p-quinodimethane, ferrocene, 1,1'-dimethyl-ferrocene, hexacyanoferrate (II) and hexacyanoferrate (III).

10. The electrochemical biosensor according to claim 1, wherein said substance capable of sorption of the chemical mediator is selected from the group consisting of silica gel, alumina, zeolites and a perfluorinated ion exchange powder prepared from a copolymer of tetrafluoroethylene and perfluoro(2-(fluorosulfonylethoxy)propyl vinyl ether.

11. The electrochemical biosensor according to claim 1, wherein said biocatalyst is an enzyme selected from the group consisting of glucose oxidase, galactose oxidase, glycolate oxidase, alcohol oxidase, cholesterol oxidase, polyphenyl oxidase, ascorbate oxidase, lipoxygenase, lopoxidase, peroxidase, catalase, xanthine oxidase, pyruvate oxidase, citrate lyase and mixtures thereof.

12. The electrochemical biosensor according to claim 1, wherein said biocatalyst is an enzyme requiring the presence of a co-factor, in association with said co-factor, said co-factor being selected from the group consisting of glucose dehydrogenase, alcohol dehydrogenase, fructose dehydrogenase, malate dehydrogenase, lactate dehydrogenase, mannitol dehydrogenase, glycerol dehydrogenase, isocitrate dehydrogenase, galactose dehydrogenase, glucose phosphate dehydrogenase, tartrate dehydrogenase and mixtures thereof.

13. The electrochemical biosensor according to claim 1, wherein said membrane is selected from the group consisting of dialysis membranes containing cellulose acetate, cellophane, nitrocellulose, polyvinyl chloride, polytetrafluoroethylene, nylon, polycarbonates, and polyesters.

14. A process for the preparation of a biosensor as described in claim 1, said process comprising the following steps:
   1) mixing an electro-conducting material with a chemical mediator;
   2) optionally mixing said mixture obtained in step (1) with a substance adsorbing said chemical mediator;

3) optionally mixing said mixture obtained in step (1) or (2) with a biocatalyst;

4) mixing said mixture obtained in step (1), (2) or (3) with a solid binding maker;

5) introducing said mixture obtained in step (4) in a suitable holder, thus obtaining a compact form;

6) when step (3) is not worked out, applying a biocatalytic layer onto the surface of said transducer obtained in step (5); and 7) optionally covering said biosensor obtained in step (5) or (6) with a suitable membrane.

15. The process according to claim 14 wherein, in step (4), said solid binding maker is mixed with said mixture obtained in step (1), (2) or (3) according to one of the following procedures:

mechanical mixing;

mixing in the presence of a solvent which is then evaporated; and melting said solid binding maker and mixing said mixture obtained in step (1), (2), or (3) with said solid binding maker in said melted state.

16. An electrochemical biosensor comprising:
a) an electro-conducting material, in the form of powder or grains;
b) a chemical mediator;
c) a substance absorbing said chemical mediator; and
d) one solid binding maker, selected from the group consisting of:
hexadecanol, hexadecanone, tetradecylamine, eicosane, tetracosane, monostearoyl glycerol, lecithin, cholesteryl myristate, cholesteryl stearate and cholesteryl oleate, said solid binding maker having a melting point comprised between 35° C. and 90° C. and said elements a)–d) constituting a composite transducer, and a biocatalyst which is a redox enzyme, and wherein said biocatalyst is either incorporated in bulk into said composite transducer or it is applied in the form of a layer onto the surface of said composite transducer, said electrochemical biosensor being optionally covered by a membrane, and wherein said electrochemical biosensor comprises, with reference to 100 parts by weight of the sum of the components (a)–(d):

a) from 30 to 60% by weight;
b) from 1 to 10% by weight;
c) from 1 to 20% by weight;
d) from 30 to 60% by weight.

17. An electrochemical biosensor comprising:
a) an electro-conducting material, in the form of powder or grains;
b) a chemical mediator;
c) a substance absorbing said chemical mediator; and
d) one solid binding maker, selected from the group consisting of:
linear or branched, saturated or unsaturated hydrocarbons, containing from 12 to 60 carbon atoms optionally substituted with at least a group selected from —OH, —SH, —$NH_2$, —CO—. —CHO, —$SO_3H$, —COOH, —$OR_1$, —$SR_1$, —$NR_1R_2$, and —$COOR_1$, wherein $R_1$ and $R_2$ are independently hydrocarbon groups, $C_1$–$C_{30}$, optionally containing one or more heteroatoms;
esters of fatty acid or a mixture of fatty acids with glycerol; and
esters of a fatty acid or a mixture of fatty acids with cholesterol, said solid binding maker having a melting point comprised between 35° C. and 90° C. and said elements a)–d) constituting a composite transducer, and a biocatalyst which is composed of cells selected from the group consisting of *Gluconobacter oxidans, Escherichia coli, Aspergillus niger, Pseudomonas fluorescens, Trichosporon brassicae, Saccharomyces cerevisiae, Breviabacterium lactofermentum, Enterobacter agglomerans, Leuconostoc mesenteroides, Nocardia erythropolys* and mixtures thereof, and wherein said biocatalyst is either incorporated in bulk into said composite transducer or it is applied in the form of a layer onto the surface of said composite transducer, said electrochemical biosensor being optionally covered by a membrane, and wherein said electrochemical biosensor comprises, with reference to 100 parts by weight of the sum of the components (a)–(d):

a) from 30 to 60% by weight;
b) from 1 to 10% by weight;
c) from 1 to 20% by weight;
d) from 30 to 60% by weight.

18. An electrochemical biosensor comprising:
an electro-conducting material, in the form of powder or grains;
a chemical mediator;
optionally, a substance adsorbing said chemical mediator;
one solid binding maker selected from the group consisting of hexadecanol, hexadecanone, tetradecylamine, eicosane, tetracosane, monostearoyl glycerol, lecithin, cholesteryl myristate, cholesteryl stearate, or cholesteryl oleate; and
a biocatalyst which is a redox enzyme, wherein said biocatalyst is either incorporated in bulk into a composite transducer or it is applied in the form of a layer onto the surface of said composite transducer, said electrochemical biosensor being optionally covered by a membrane.

19. A process for the preparation of a biosensor as described in claim 18, said process comprising the following steps:

1) mixing an electro-conducting material with a chemical mediator;

2) optionally mixing said mixture obtained in step (1) with a substance adsorbing said chemical mediator;

3) optionally mixing said mixture obtained in step (1) or (2) with a biocatalyst;

4) mixing said mixture obtained in step (1), (2) or (3) with a solid binding maker;

5) introducing said mixture obtained in step (4) in a suitable holder, thus obtaining a compact form;

6) when step (3) is not worked out, applying a biocatalytic layer onto the surface of said transducer obtained in step (5); and 7) optionally covering said biosensor obtained in step (5) or (6) with a suitable membrane.

20. The process according to claim 19 wherein, in step (4), said solid binding maker is mixed with said mixture obtained in step (1), (2) or (3) according to one of the following procedures:

mechanical mixing;

mixing in the presence of a solvent which is then evaporated; and melting said solid binding maker and mixing said mixture obtained in step (1), (2), or (3) with said solid binding maker in said melted state.

21. An electrochemical biosensor comprising:
a) an electro-conducting material, in the form of powder or grains;
b) a chemical mediator;
c) optionally, a substance adsorbing said chemical mediator;
d) one solid binding maker, selected from the group of:
linear or branched, saturated or unsaturated hydrocarbons, containing from 12 to 60 carbon atoms optionally substituted with at least a group selected from —OH, —SH, —$NH_2$, —CO—, —CHO, —$SO_3H$, —COOH, —$OR_1$, —$SR_1$, —$NR_1R_2$ and —$COOR_1$, wherein $R_1$ and $R_2$ are independently hydrocarbon groups $C_1$–$C_{30}$, optionally containing one or more heteroatoms;
esters of a fatty acid or a mixture of fatty acids with glycerol; and
esters of a fatty acid or a mixture of fatty acids with cholesterol, said solid binding maker having a melting point comprised between 35° C. and 90° C. and said elements a)–d) constituting a composite transducer, and a biocatalyst composed of cells selected from the group consisting of *Gluconobacter oxidans, Escherichia coli, Aspergillus niger, Pseudomonas fluorescens, Trichosporon brassicae, Saccharomyces cerevisiae, Breviacterium lactofermentum, Enterobacter agglomerans, Leuconostoc mesenteroides, Nocardia erythropolys* and mixtures thereof.

22. A process for the preparation of a biosensor as described in claim 21, said process comprising the following steps:
1) mixing an electro-conducting material with a chemical mediator;
2) optionally mixing said mixture obtained in step (1) with a substance adsorbing said chemical mediator;
3) optionally mixing said mixture obtained in step (1) or (2) with a biocatalyst;
4) mixing said mixture obtained in step (1), (2) or (3) with a solid binding maker;
5) introducing said mixture obtained in step (4) in a suitable holder, thus obtaining a compact form;
6) when step (3) is not worked out, applying a biocatalytic layer onto the surface of said transducer obtained in step (5); and
7) optionally covering said biosensor obtained in step (5) or (6) with a suitable membrane.

23. The process according to claim 22 wherein, in step (4), said solid binding maker is mixed with said mixture obtained in step (1), (2) or (3) according to one of the following procedures:
mechanical mixing;
mixing in the presence of a solvent which is then evaporated; and
melting said solid binding maker and mixing said mixture obtained in step (1), (2), or (3) with said solid binding maker in said melted state.

24. The electrochemical biosensor according to claim 12, wherein said co-factor is selected from the group consisting of NAD, NADH, NADP, NADPH, FAD, FMN and quinone.

* * * * *